US011105809B2

(12) United States Patent
Fishelson et al.

(10) Patent No.: US 11,105,809 B2
(45) Date of Patent: Aug. 31, 2021

(54) METHODS AND KITS FOR PREDICTING PROGNOSIS OF CANCER USING SOLUBLE MORTALIN IN BLOOD

(71) Applicant: Ramot at Tel-Aviv University Ltd., Tel-Aviv (IL)

(72) Inventors: Zvi Fishelson, Tel-Aviv (IL); Zoltan Prohaszka, Budapest (HU)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 459 days.

(21) Appl. No.: 14/434,164

(22) PCT Filed: Oct. 9, 2013

(86) PCT No.: PCT/IL2013/050817
§ 371 (c)(1),
(2) Date: Apr. 8, 2015

(87) PCT Pub. No.: WO2014/057490
PCT Pub. Date: Apr. 17, 2014

(65) Prior Publication Data
US 2015/0268242 A1 Sep. 24, 2015

Related U.S. Application Data

(60) Provisional application No. 61/711,327, filed on Oct. 9, 2012.

(51) Int. Cl.
*G01N 31/00* (2006.01)
*G01N 33/53* (2006.01)
*G01N 33/574* (2006.01)

(52) U.S. Cl.
CPC . *G01N 33/57488* (2013.01); *G01N 33/57407* (2013.01); *G01N 33/57419* (2013.01); *G01N 2333/4703* (2013.01)

(58) Field of Classification Search
CPC ............... C12Q 1/6811; C12Q 1/6886; G01N 33/57488; C12N 15/115; C12N 2310/16
See application file for complete search history.

(56) References Cited

U.S. PATENT DOCUMENTS

| | | | | |
|---|---|---|---|---|
| 5,627,039 | A * | 5/1997 | Pereira-Smith | G01N 33/57496 435/7.23 |
| 7,700,307 | B2 * | 4/2010 | Murray | G01N 33/57419 435/7.23 |
| 7,883,702 | B2 | 2/2011 | Wadhwa et al. | |
| 8,293,716 | B2 * | 10/2012 | Fishelson | C07K 16/18 514/44 A |
| 8,470,793 | B2 * | 6/2013 | Fishelson | A61K 31/713 424/138.1 |
| 2006/0270622 | A1 | 11/2006 | Fishelson et al. | |
| 2009/0023657 | A1 | 1/2009 | Gabriele et al. | |

FOREIGN PATENT DOCUMENTS

| | | | | |
|---|---|---|---|---|
| EP | 1243923 A1 * | 9/2002 | ........ | G01N 33/5011 |
| WO | WO 2004/079368 | 9/2004 | | |
| WO | WO 2007/071045 | 6/2007 | | |
| WO | WO 2008/032324 | 3/2008 | | |
| WO | WO 2009/040819 | 4/2009 | | |
| WO | WO 2011/071099 | 6/2011 | | |
| WO | WO 2013/190075 | 12/2013 | | |
| WO | WO 2014/057490 | 4/2014 | | |

OTHER PUBLICATIONS

Iosefson et al. (Cell Stress and Chaperones, Jan. 2012, vol. 17, pp. 57-66).*
Iosefson et al. (Cell Stress and Chaperones, vol. 17, pp. 57-66, 2012).*
StressMarq Biosciences Inc., Victoria Canada Product Sheet 2018.*
Santa Cruz Biotechnology, Santa Cruz, CA, Product Sheet, 2018.*
Santa Cruz Biotechnology, Santa Cruz, CA, Product List, 2018.*
Iosefson et al. (Cell Stress and Chaperones, 2012, vol. 17, pp. 57-66).*
Molvarec et al. (Journal of Human Hypertension, vol. 20, pp. 780-786, 2006) (Year: 2006).*
Wadhwa et al. (Biochem J. vol. 391, pp. 185-190, 2005) (Year: 2005).*
Kocsis et al. (Cell Stress & Chaperones, Mar. 2010, vol. 15, No. 2, pp. 143-151) (Year: 2010).*
Srokowski et al. "Expression and Localization of GRP75 in Human Epithelial Tumors and Normal Tissues", Applied Immunohistochemistry & Molecular Morphology, XP008179660, 12(2): 132-138, Jun. 2004. Title, Abstract, Materials and Method Section, Figs.3, 4.
International Preliminary Report on Patentability dated Apr. 23, 2015 From the International Bureau of WIPO Re. Application No. PCT/IL2013/050817.
International Search Report and the Written Opinion dated Dec. 29, 2013 From the International Searching Authority Re. Application No. PCT/IL2013/050817.
Czarnecka et al. "Mitochondrial Chaperones in Cancer. From Molecular Biology to Clinical Diagnostics", Cancer Biology & Therapy, 5(7): 714-720, Jul. 31, 2006.
De Maio "Extracellular Heat Shock Proteins, Cellular Export Vesicles, and the Stress Observation System: A Form of Communication During Injury, Infection, and Cell Damage", Cell Stress and Chaperones, 16: 235-249, Published Online Oct. 21, 2010.
Dundas et al. "Mortalin Is Over-Expressed by Colorectal Adenocarcinomas and Correlates With Poor Survival", Journal of Pathology, 205(1): 74-81, Mar. 31, 2005. Abstract.

(Continued)

*Primary Examiner* — Lisa V Cook

(57) ABSTRACT

Provided are methods of determining a presence or level of soluble mortalin in a body fluid of a subject, and predicting prognosis of a subject diagnosed with cancer (e.g., solid tumor) by determining the presence or level of soluble mortalin in a body fluid of the subject. Also provided are kits for determining presence and/or level of soluble mortalin in a body fluid of the subject and/or predicting prognosis of a subject diagnosed with cancer, comprising at least two distinct antibodies to mortalin directed against different epitopes of said mortalin.

11 Claims, 3 Drawing Sheets

Specification includes a Sequence Listing.

(56) References Cited

OTHER PUBLICATIONS

Kocsis et al. "High Levels of Acute Phase Proteins and Soluble 70 kDa Heat Shock Proteins Are Independent and Additive Risk Factors for Mortality in Colorectal Cancer", Cell stress and Chaperones, 16: 49-55, Published Online Aug. 22, 2010.

Kocsis et al. "Serum Level of Soluble 70-kD Heat Shock Protein Is Associated With High Mortality in Patients With Colorectal Cancer Without Distant Metastasis", Cell Stress and Chaperones, 15: 143-151, Published Online Jul. 4, 2009.

Kocsis et al. "Serum Level of Soluble 70-kD Heat Shock Protein Is Associated With High Mortality in Patients With Colorector Cancer Without Distant Metastasis", Cell Stress and Chaperones, 15: 143-151, Published Online Jul. 4, 2009.

Koji et al. "Significance of Mortalin Expression in Gastric Cancer With Normal P53", General Poster Session A: Cancers of the Esophagus and Stomach, 2012 Gastrointestinal Cancers Symposium, Jul. 31, 2012, Journal of Clinical Oncology, 30(Suppl.4): # 25, Jul. 31, 2012.

Pilzer et al. "Emission of Membrane Vesicles: Roles in Complement Resistance, Immunity and Cancer", Springer Seminars in Immunopathology, 27(3): 375-387, Nov. 2005.

Pilzer et al. "Mortalin Inhibitors Sensitize K562 Leukemia Cells to Complement-Dependent Cytotoxicity", International Journal of Cancer, 126: 1428-1435, 2010.

Pilzer et al. "Mortalin/GRP75 Promotes Release of Membrane Vesicles From Immune Attacked Cells and Protection From Complement-Mediated Lysis", International Immunology, 17(9): 1239-1248, Aug. 9, 2005.

Rozenberg et al. "Elevated Levels of Mitochondrial Mortalin and Cytosolic HSP70 in Blood as Risk Factors in Patients With Colorectal Cancer", International Journal of Cancer, 133(2): 514-518, Jul. 15, 2013. Abstract. Abstract.

Takano et al. "Elevated Levels of Mortalin Expression in Human Brain Tumors", Experimental Cell Research, 237: 38-45, 1997.

Yi et al. "Association of Mortalin (HSPA9) With Liver Cancer Metastasis and Prediction for Early Tumor Recurrence", Molecular & Cellular Proteomics, 7(2): 315-325, 2008.

* cited by examiner

METHODS AND KITS FOR PREDICTING PROGNOSIS OF CANCER USING SOLUBLE MORTALIN IN BLOOD

RELATED APPLICATIONS

This application is a National Phase of PCT Patent Application No. PCT/IL2013/050817 having International filing date of Oct. 9, 2013, which claims the benefit of priority under 35 USC § 119(e) of U.S. Provisional Patent Application No. 61/711,327 filed on Oct. 9, 2012. The contents of the above applications are all incorporated by reference as if fully set forth herein in their entirety.

SEQUENCE LISTING STATEMENT

The ASCII file, entitled 62212SequenceListing.txt, created on Mar. 24, 2015, comprising 48,340 bytes, submitted concurrently with the filing of this application is incorporated herein by reference.

FIELD AND BACKGROUND OF THE INVENTION

The present invention, in some embodiments thereof, relates to methods and kits for determining the presence and/or level of mortalin in a biological sample such body fluids of a subject, e.g., blood, and methods and kits for determining prognosis of a subject having a solid cancerous tumor, e.g., colorectal cancer, based on the level of mortalin in the biological sample (e.g., blood).

Mortalin (mthsp70/grp75), the mitochondrial heat shock protein 70, plays a major role in import and refolding of mitochondrial proteins. Mortalin is ubiquitously and constitutively expressed in all eukaryotic cells and its expression is not heat-induced, yet may be affected following ionizing radiation, glucose deprivation and calorie restriction. Mortalin is essential for cell growth and mitochondrial biogenesis. Over expression of mortalin protected cells from glucose deprivation and reactive oxygen species (ROS) accumulation and from serum deprivation, reduced oxidative stress, antagonized ischemic damage and promoted tumorigenesis. In contrast, knock down of mortalin by RNA interference caused senescence-like growth arrest in immortalized cells. Synthesized with a mitochondrial-targeting sequence, mortalin is mainly located in mitochondria, yet few reports identified it in other cellular compartments such as the cytosol and plasma membrane.

Several human transformed and tumor cells have been shown to express elevated levels of mortalin (14). In human colorectal adenocarcinoma, higher mortalin expression in situ (in tumors) correlated with poor patient survival (15). Mortalin plays a role in protection of cancer cells from complement-dependent cytotoxicity (16, 17) and it facilitates elimination of the complement membrane attack complex (MAC) from the cell surface by exo-vesiculation (16). Mortalin inhibitors sensitized the cells to complement-dependent cytotoxicity and inhibited the shedding of mortalin with the MAC (17).

Contrary to mortalin, the cytosolic hsp70 (also referred to as "sHSP70" hereinafter) was known to be released from cells (19), and was identified in blood plasma of patients with colorectal cancer (20). sHSP70 was found to be a useful, stage-independent prognostic marker in colorectal cancer, especially in patients without distant metastasis. Plasma levels of sHSP70 and acute phase proteins could independently predict survival in patients with colorectal cancer but their combined measurements gave even a higher prediction value in specific subgroups of patients (21).

Additional related art include Pilzer, D., and Z. Fishelson. 2005 (Int Immunol 17:1239-1248); Pilzer, D., et al., 2005 (Springer Semin Immunopathol 27:375-387); WO2008032324 and WO2009/040819.

SUMMARY OF THE INVENTION

According to an aspect of some embodiments of the present invention there is provided a method of predicting prognosis of a subject diagnosed with cancer (e.g., a solid tumor), comprising: determining presence and/or level of soluble mortalin in a body fluid of the subject, wherein
(i) when a level of the soluble mortalin is above a predetermined threshold, then the subject is predicted to have poor prognosis as compared to an expected prognosis based on the subject's tumor stage, age and/or gender; and
(ii) when a level of the soluble mortalin is below a predetermined threshold, then the subject has good prognosis as compared to an expected prognosis based on the subject's tumor stage, age and/or gender,
thereby predicting the prognosis of the subject diagnosed with the cancer (e.g., the solid tumor).

According to an aspect of some embodiments of the present invention there is provided a method of analyzing a presence and/or level of soluble mortalin in a biological sample (e.g., body fluid) of a subject, comprising: determining a presence or level of soluble mortalin in the biological sample, thereby analyzing the soluble mortalin in the biological sample (e.g., the body fluid) of the subject.

According to an aspect of some embodiments of the present invention there is provided a kit for determining presence and/or level of soluble mortalin in a biological sample (e.g., body fluid) of a subject and/or predicting prognosis of a subject diagnosed with a solid tumor, comprising: at least two distinct antibodies to mortalin directed against different epitopes of the mortalin.

According to some embodiments of the invention, the method of some embodiments of the invention, further comprising:
classifying the subject as having good or poor prognosis based on the level of the soluble mortalin, thereby predicting the prognosis of the subject diagnosed with the cancer (e.g., the solid tumor).

According to some embodiments of the invention, determining the presence or the level of the soluble mortalin is effected using an immunological method or a mass-spectroscopy.

According to some embodiments of the invention, the immunological method comprising:
(a) contacting the biological sample (e.g., body fluid) with an anti-mortalin antibody under conditions which allow immunocomplex formation; and
(b) determining a presence or level of the immunocomplex,
thereby determining the presence or the level of the soluble mortalin in the biological sample (e.g., body fluid).

According to some embodiments of the invention, the anti-mortalin antibody is bound to a solid support.

According to some embodiments of the invention, a presence or level of the immunocomplex is determined by surface plasmon resonance.

According to some embodiments of the invention, a presence or level of the immunocomplex is determined by Enzyme-linked immunosorbent assay (ELISA).

According to some embodiments of the invention, the soluble mortalin is not attached to a cell, to a cell membrane, or to a cell organelle.

According to some embodiments of the invention, wherein when the solid tumor is colorectal cancer, then the poor prognosis is characterized about 43 months mean survival time.

According to some embodiments of the invention, wherein when the solid tumor is colorectal cancer, then the good prognosis is characterized about 72 months mean survival time.

According to some embodiments of the invention, the method of some embodiments of the invention, further comprising:

(a) determining the level of soluble heat shock protein 70 (sHSP70) in the biological sample (e.g., the body fluid), wherein when a level of the soluble mortalin and the sHSP70, each is above a predetermined threshold in the biological sample (e.g., the body fluid), then the subject is predicted to have a poor prognosis as compared to an expected prognosis based on the subject's tumor's stage, age and/or gender; and (b) classifying the subject as having good or poor prognosis based on the mortalin and the sHSP70 level, thereby predicting the prognosis of the subject diagnosed with the solid tumor.

According to some embodiments of the invention, the kit of some embodiments of the invention, further comprising a secondary antibody for binding one of the at least two antibodies.

According to some embodiments of the invention, the kit of some embodiments of the invention, further comprising an Enzyme-linked immunosorbent assay (ELISA) plate.

According to some embodiments of the invention, the kit of some embodiments of the invention, further comprising an anti-soluble heat shock protein 70 (sHSP70) antibody.

According to some embodiments of the invention, the biological sample (e.g., the body fluid) is selected from the group consisting of blood, urine, tear, saliva, stool, cerebrospinal fluid, synovial fluid, lymph fluids, external secretions of a respiratory tract, external secretions of an intestinal tract external secretions of a genitourinary tract, milk, amniotic fluid and chorionic villi.

According to some embodiments of the invention, the blood sample comprises serum.

According to some embodiments of the invention, the biological sample (e.g., the body fluid) is a serum sample of the subject.

According to some embodiments of the invention, the solid tumor comprises colorectal cancer.

According to some embodiments of the invention, the immunocomplex is employed in an immunoprecipitation assay.

According to some embodiments of the invention, the immunoprecipitation assay is followed by mass spectroscopy or nephelometry.

According to some embodiments of the invention, one antibody of the at least two antibodies is a mouse monoclonal against human mortalin.

According to some embodiments of the invention, one antibody of the at least two antibodies is a goat polyclonal against human mortalin.

According to some embodiments of the invention, the mouse monoclonal antibody against human mortalin is attached to a solid support.

According to some embodiments of the invention, the kit further comprising a calibration standard for mortalin levels.

According to some embodiments of the invention, the level of the mortalin immunocomplex is between about 10 nanogram per milliliter (ng/ml) to about 214 ng/ml.

According to some embodiments of the invention, the predetermined threshold is about 60 ng/ml of mortalin in the biological sample (e.g., body fluid).

According to some embodiments of the invention, the predetermined threshold is about 60 ng/ml of mortalin in the serum.

According to some embodiments of the invention, the tumor stage is determined by Classification of Malignant Tumours (TNM) criteria.

According to some embodiments of the invention, the TNM is TNM-T based on tumor size and state of invasion to nearby tissue.

According to some embodiments of the invention, the TNM is TNM-N based on extent of lymph node involvement.

According to some embodiments of the invention, the TNM is TNM-M based on presence or absence of distant metastases.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how to embodiments of the invention may be practiced.

In the drawings.

DESCRIPTION OF SPECIFIC EMBODIMENTS OF THE INVENTION

The present invention, in some embodiments thereof, relates to methods and kits for determining the presence and/or level of mortalin in a biological sample (e.g., a body fluid of a subject) such as blood (e.g., serum), and methods and kits for determining prognosis of a subject having a solid cancerous tumor, e.g., colorectal cancer, based on the level of mortalin in the biological sample (e.g., the body fluid such as blood or serum).

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have uncovered, following laborious experimentations, a novel and sensitive method for determining the presence and level of mortalin in a biological sample (e.g., body fluids of the subject) such as blood, e.g., serum. By using this ELISA the present inventors have identified mortalin in serum of colorectal cancer patients, and found that higher levels of mortalin in the serum of the patients correlates with faster disease progression and shorter survival time of the patients having colorectal cancer.

Figure 1:
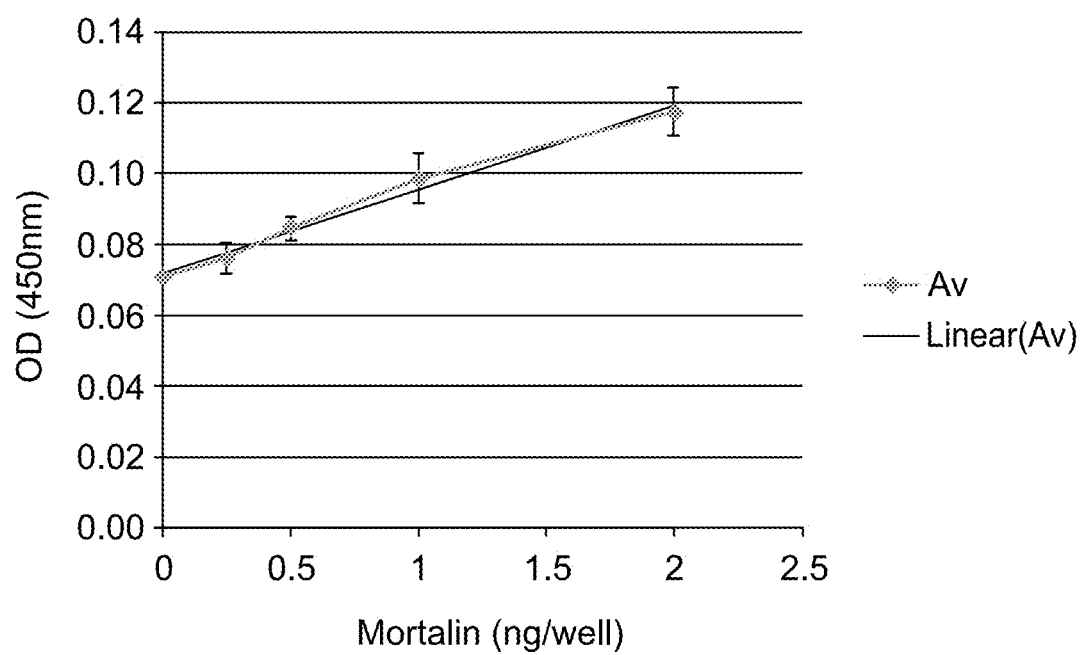
FIG. 1 is a calibration curve of mortalin ELISA. Recombinant human mortalin (0.25-2.0 ng per well) was analyzed by the capture ELISA described under Methods. The calibration curve was used to quantify the amount of mortalin in patients' sera.
Figure 2:
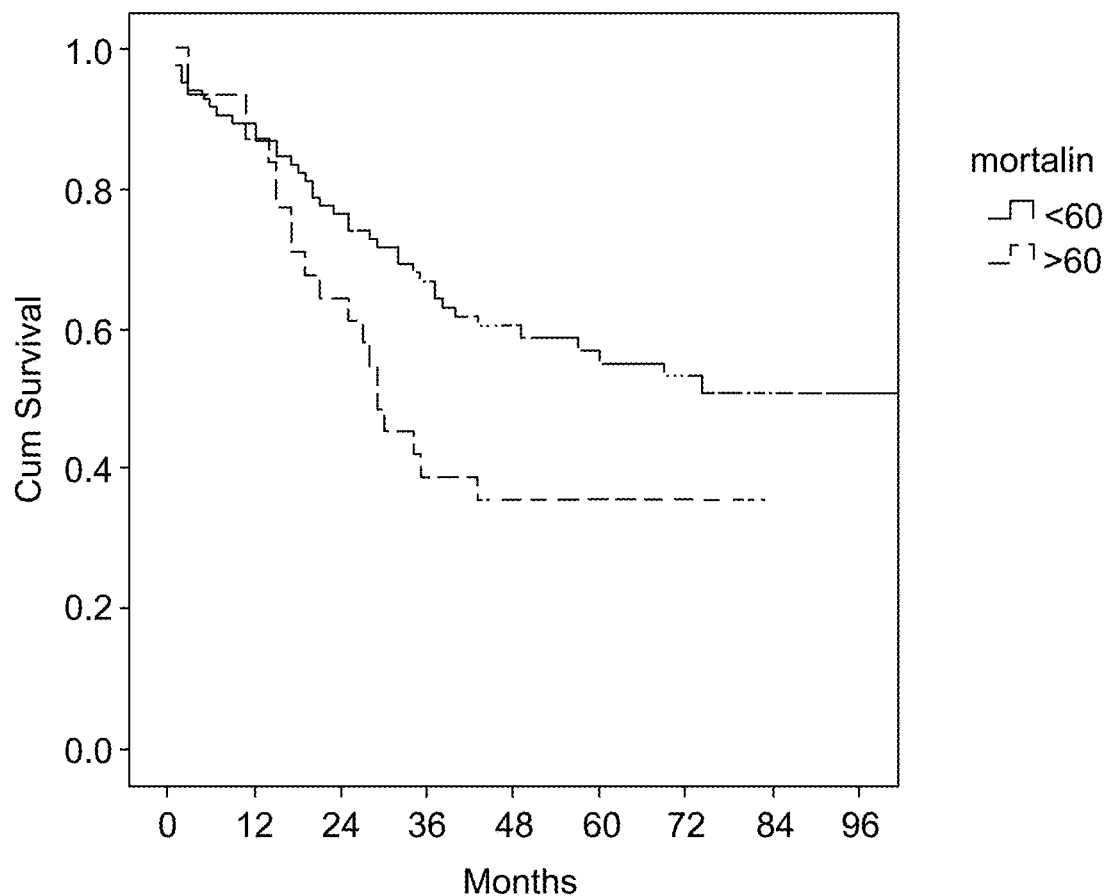
FIG. 2 is a graph depicting cumulative survival (Kaplan-Meier) of colorectal cancer patients. Patients divided according to mortalin levels in their serum; high (≥60 ng/ml) or low (<60 ng/ml) mortalin in their serum. Log Rank overall comparison showed significant equality of survival distribution (P=0.042). Table 1 (Examples section below) provides the survival data of the patients presented in this Figure.
Figure 4:
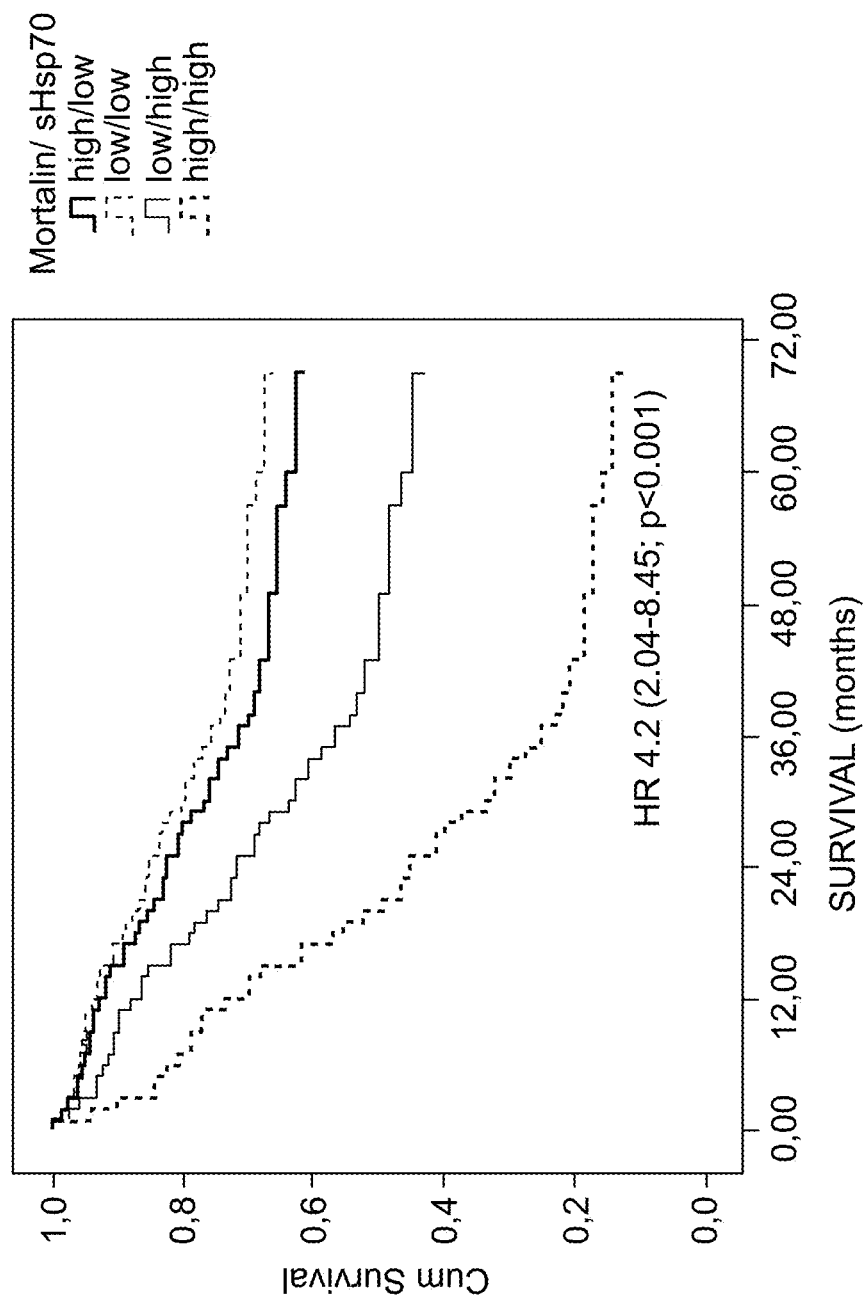
FIG. 4 is a graph depicting cumulative survival of the colorectal cancer patients divided according to their mortalin (low: <60 ng/ml, high: >60 ng/ml) and sHSP70 (low: <1.65 ng/ml., high: >1.65 ng/ml) levels. Analysis by Cox regression HR (with 95% CI) of patients with both high mortalin and high HSP70 vs. both low mortalin and low sHSP70 is indicated. Table 4 (Examples section below) provides the survival data of the patients presented in this Figure.

Thus, as shown in the Examples section which follows, the novel ELISA method is based on the combination of two anti-mortalin antibodies which are added sequentially, such that a highly sensitive detection of mortalin levels is obtained in a biological sample (Examples 1 of the Examples section which follows and FIG. 1). Using this method, the level of mortalin in serum samples of colorectal cancer patients was determined and was found to be between 14-215 ng/ml (Example 2 of the Examples section which follows). The samples of colorectal cancer patients were then divided based on Receiver operating characteristic (ROC) calculation to yield optimal stratification of patients regarding mortalin levels and survival. Thus, colorectal patients having serum mortalin levels which are below 60 ng/ml (also referred to as "low mortalin" levels hereinafter) were compared to those having a mortalin level which is equal or higher than 60 ng/ml (also referred to as "high mortalin" levels hereinafter). As shown in Example 2 of the Examples section which follows, a significant correlation (R=0.335, p<0.001) was found between serum mortalin and C1-Inhibitor concentrations. In addition, univariate survival analysis revealed mortalin as a predictor for patient's survival (Example 3 of the Examples section which follows) with 113 months estimated median survival in the "low mortalin" group and 29 months median survival in the "high mortalin" group (FIG. 2 and Table 1). Moreover, multivariate analysis in which the survival of the patients stratified according to sHSP70 and mortalin levels was analyzed (FIG. 4 and Table 4) revealed that patients with concomitant high mortalin and high sHSP70 concentrations (>1.67 ng/ml) had a 4.2 times higher hazard of mortality than patients with both low sHSP70 and low mortalin levels, indicating the additive nature of these two biomarkers (FIG. 4). Median survival time of the patients with high mortalin/high sHSP70 and low mortalin/low sHSP70 levels were 27.5 (13.3-34.3) months and 57.0 (31.0-81.0) months, respectively. In addition, the mean survival time (FIG. 4) of patients with high mortalin/high sHsp70 was 24.9±14.0 months and that of patients with low mortalin/low sHsp70 was 54.6±30.8 months. In addition, as described in Example 3 of the Examples section which follows and in Table 5, the addition of the biomarkers sHsp70 and mortalin to the baseline model which includes the basic demographic variables and tumor stage significantly increased the survival-predicting value of the model (the likelihood-ratio test, $\chi^2=26.846$; p<0.001). In the subgroup of patients with concomitantly high sHsp70 and mortalin levels, a hazard rate of 8.176 (95% CI 3.267-20.463, P<0.001) was observed, indicating that the baseline model (clinical stage, age and sex) and the biomarkers are independent and additive predictors of mortality in colorectal cancer. The hazard index was found to be very high when levels of both mortalin and sHSP70 in serum were elevated and even higher when combined with the TNM cancer stage. Altogether, these findings demonstrate the development of novel and sensitive methods of determining presence and/or level of mortalin in a sample and using these methods for predicting prognosis of a subject having cancer.

Thus, according to an aspect of some embodiments of the invention, there is provided a method comprising determining a presence and/or level of soluble mortalin in a body fluid of a subject.

The term "mortalin" refers to the heat shock 70 KDa protein 9 (HSPA9). Preferably, the mortalin is human mortalin, which is also known as CSA; MOT; MOT2; PBP74; GRP75; HSPA9B; MTHSP75, and encodes a member of the heat shock protein 70 gene family. The encoded protein is primarily localized to the mitochondria but is also found in the endoplasmic reticulum, plasma membrane and cytoplasmic vesicles. This protein is a heat-shock cognate protein, which plays a role in cell proliferation, stress response and maintenance of the mitochondria. The human mortalin polypeptide is set forth in SEQ ID NO:1 (GenBank Accession NO. NP_004125.3). The human mortalin mRNA is provided in SEQ ID NO:2 (GenBank Accession No. NM_004134, (gi|296080701, nuclear gene encoding mitochondrial protein, mRNA).

According to some embodiments of the invention, the soluble mortalin is set forth in SEQ ID NO:1.

As used herein the term "soluble" mortalin refers to a mortalin polypeptide which is at least partially separated from any cellular moiety such as a cell membrane, a nuclear membrane, cytoplasmic vesicles, cell organelle, e.g., mitochondria, endoplasmic reticulum, Golgi apparatus, lysosomes, nucleus and the like.

According to some embodiments of the invention, the soluble mortalin is not attached to a cell, to a cell membrane or to a cell organelle.

According to some embodiments of the invention, the mortalin is a circulating soluble mortalin which is not attached to a cell or to any cellular moiety such as those described above.

According to some embodiments of the invention, the soluble mortalin is not present on, in or attached to a solid cancerous tumor.

According to some embodiments of the invention, the method is performed in vitro.

According to some embodiments of the invention, the method is performed ex vivo.

According to some embodiments of the invention, the biological sample is a bodily fluid (body fluid of the subject) such as whole blood, serum, plasma, cerebrospinal fluid, synovial fluid, urine, lymph fluids, and various external secretions of the respiratory, intestinal and genitourinary tracts, tears, saliva, milk as well as white blood cells, amniotic fluid and chorionic villi.

Methods of obtaining body fluids of a subject are well known in the art an include for example, collection of urine, saliva and tears, aspiration of cerebrospinal fluid, synovial fluid, lymph fluids, and various external secretions of the respiratory, intestinal and genitourinary tracts, the use of a needle and/or a catheter for drawing a to blood sample, amniotic fluid sample, chorionic villi sample and the like from the subject.

According to some embodiments of the invention, the body fluid is at least partially removed from the subject.

According to some embodiments of the invention, the body fluid is removed from the subject (e.g., completely separated from the subject).

According to some embodiments of the invention, the body fluid is taken from the subject using a non-invasive method.

According to some embodiments of the invention, the body fluid is an archival sample of the subject.

According to some embodiments of the invention, the body fluid is a clinical sample available from the subject.

According to some embodiments of the invention, the biological sample is a cell suspension of body fluids.

According to some embodiments of the invention, the blood sample can be whole blood, serum, and/or plasma.

According to some embodiments of the invention, the biological sample is a blood sample, e.g., a serum sample.

According to some embodiments of the invention, the blood sample is a serum sample.

According to some embodiments of the invention, the blood sample is a non-cultured blood sample obtained from a subject.

According to some embodiments of the invention, the blood sample comprises supernatant collected from in vitro cultured blood cells.

According to some embodiments of the invention, the biological sample (e.g., body fluid) is not a sample of a solid tumor (e.g., tissue biopsy of a solid tumor, fine needle aspirate of a solid tumor).

According to some embodiments of the invention, the biological sample (e.g., body fluid) is obtained from a subject having a solid cancerous tumor.

As used herein the term "subject" refers to a mammal, e.g., a human being. The subject can be a male or a female at any age.

According to some embodiments of the invention, the subject is diagnosed with a solid cancerous tumor.

According to some embodiments of the invention, the cancer is any solid tumor and/or cancer metastasis thereof, including, but not limited to, tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic; breast cancer, susceptibility to breast cancer, type 4 breast cancer, breast cancer-1, breast cancer-3; breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B cell), hypernephroma, insulinoma, islet tumor, keratoma, leiomyoblastoma, leiomyosarcoma, leukemia (e.g., acute lymphatic, acute lymphoblastic, acute lymphoblastic pre-B cell, acute lymphoblastic T cell leukemia, acute-megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme; multiple glomus tumors, Li-Fraumeni syndrome, liposarcoma, lynch cancer family syndrome II, male germ cell tumor, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

According to some embodiments of the invention, the cancer is colorectal cancer.

According to specific embodiments of the invention, the subject does not have a non-solid tumor (e.g., leukemia).

As used herein the phrase "determining a presence . . . " refers to the determination of presence or absence of mortalin in the sample as assayed by a method such as ELISA, Western blot analysis, radio immunoassay (RIA), Fluorescence activated cell sorting (FACS), surface plasmon resonance, immunohistochemistry, immunofluorescence, immunoprecipitation, nephelometry and mass spectroscopy when compared to a negative control sample which is devoid of mortalin.

According to some embodiments of the invention, determining the presence and/or the level of the soluble mortalin is effected by a method selected from the group consisting of an immunological assay, mass-spectroscopy, nephelometry and surface Plasmon resonance.

According to some embodiments of the invention, determining the presence and/or the level of the soluble mortalin is effected using an immunological method or a mass-spectroscopy method.

The mass spectroscopy detects peptide sequences and is able to identify the presence of a protein in a sample.

For example, for mass spectroscopy, the samples are trypsinized and the tryptic peptides are analyzed by Liquid Chromatography-Mass Spectrometry (LC-MSMS) on the Orbitrap mass spectrometer (Thermo). The data can be analyzed using the Sequest 3.31 software versus the e coli section of the NCBI-NR (non-redundant National Center for Biotechnology Information) database and versus the whole Uniprot database and vs the human section of it. Thus, mass spectroscopy analysis can detect presence of mortalin in a sample and further determine the level of mortalin in the sample.

According to some embodiments of the invention, determining the presence and/or the level of the soluble mortalin is effected by an immunological detection assay or method.

According to an aspect of some embodiments of the invention, the method of determining presence or level of soluble mortalin in a biological sample (e.g., body fluid) of a subject is effected by: (a) contacting the biological sample with an anti-mortalin antibody under conditions which allow immunocomplex formation; and (b) determining a presence or level of the immunocomplex, thereby determining the presence and/or level of the soluble mortalin in the biological sample.

According to some embodiments of the invention, determining the presence or level of mortalin is performed using a mortalin specific antibody or antibodies which are added (or applied) to a sample of body fluid of the subject, e.g., anti-mortalin antibodies which are added to a serum sample of a subject and form an immunocomplex.

As used herein the term "immunological" refers to using an antigen-antibody interaction, by formation of an immunocomplex, in order to determine presence and/or level of mortalin.

As used herein the phrase "immunocomplex" refers to a complex formed by binding of an antibody to its antigen.

According to some embodiments of the invention, binding of the antibody to the antigen depends on affinity between the antibody to an epitope on or in the antigen.

According to some embodiments of the invention, the complex is a non-covalent complex.

As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720[. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778], which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies [Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

According to some embodiments of the invention, the anti-mortalin antibody is a monoclonal antibody.

Commercially available monoclonal anti-mortalin antibodies include, but are not limited to mouse monoclonal antibody directed to human mortalin (StressMarq Biosciences Inc., Victoria, Canada), mouse monoclonal anti-human mortalin (Enzo® Life Sciences, Cat. No. ADI-SPS-825), and Rabbit Anti-Mortalin antibody (Monoclonal, Cell Signaling Technology [D13H4] Cat. No. 3593P).

According to some embodiments of the invention, the anti-mortalin antibody is a polyclonal antibody.

Commercially available polyclonal anti-mortalin antibodies include, but are not limited to and treated with a goat anti-human mortalin polyclonal antibody (Santa Cruz Biotechnology, Santa Cruz, Calif.); rabbit polyclonal anti-mortalin (Enzo® Life Sciences, Catalogue Number ADI-SPS-827-D); Rabbit Anti-Mortalin antibody, Polyclonal Cell Signaling Technology Cat. No. 2816S.

According to some embodiments of the invention, the anti-mortalin antibody comprises a combination of at least two anti-mortalin antibodies, each binding to a different epitope of mortalin. For example, a mouse monoclonal antibody and a goat polyclonal antibody. For example, the mouse monoclonal antibody available from StressMarq can be used, along with the Goat polyclonal antibody, available from Santa Cruz.

The antibody or antibody fragment may be attached to any of various functional moieties. An antibody or antibody fragment, such as that of some embodiments of the invention, attached to a functional moiety may be referred to in the art as an "immunoconjugate".

According to some embodiments of the invention, the functional moiety is a detectable moiety or a toxin.

The detectable moiety attached to the antibody or antibody fragment can be a reporter moiety enabling specific detection of the immunocomplex.

While various types of reporter moieties may be utilized to detect the immunocomplex, depending on the application and purpose, the reporter moiety can be a fluorophore or an enzyme. Alternately, the reporter moiety may be a radioisotope, such as [125]iodine. Further examples of reporter moieties, including those detectable by Positron Emission Tomagraphy (PET) and Magnetic Resonance Imaging (MRI), are well known to those of skill in the art.

A fluorophore may be advantageously employed as a detection moiety enabling detection of the immunocomplex via any of numerous fluorescence detection methods. Depending on the application and purpose, such fluorescence detection methods include, but are not limited to, fluorescence activated flow cytometry (FACS), immunofluorescence confocal microscopy, fluorescence in-situ hybridization (FISH), fluorescence resonance energy transfer (FRET), and the like.

Various types of fluorophores, depending on the application and purpose, may be employed to detect the immunocomplex.

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), TEXAS RED (MOLECULAR PROBES, INC. sulforhodamine 101 acid chloride), PE-Cy5, and the like.

Preferably, the fluorophore is phycoerythrin.

Ample guidance regarding fluorophore selection, methods of linking fluorophores to various types of molecules, such as an antibody or antibody fragment of the invention, and methods of using such conjugates to detect molecules which are capable of being specifically bound by antibodies or antibody fragments comprised in such immunoconjugates is available in the literature of the art [for example, refer to: Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, UK. (2001); U.S. Pat. No. 6,350,466 to Targesome, Inc.].

Alternately, an enzyme may be advantageously utilized as the detectable moiety to enable detection of the immunocomplex via any of various enzyme-based detection methods. Examples of such methods include, but are not limited to, enzyme linked immunosorbent assay (ELISA; for example, to detect the immunocomplex in a solution), enzyme-linked chemiluminescence assay (for example, to detect the immunocomplex in an electrophoretically separated protein mixture), and enzyme-linked immunohistochemical assay (for example, to detect the immunocomplex in a fixed tissue).

Numerous types of enzymes may be employed to detect the immunocomplex, depending on the application and purpose. For example, an antibody or antibody fragment attached to an enzyme such as horseradish peroxidase can be used to effectively detect the immunocomplex, such as via ELISA, or enzyme-linked immunohistochemical assay.

Examples of suitable enzymes include, but are not limited to, horseradish peroxidase (HPR), beta-galactosidase, and alkaline phosphatase (AP).

Ample guidance for practicing such enzyme-based detection methods is provided in the literature of the art (for example, refer to: Khatkhatay M I. and Desai M., 1999. J Immunoassay 20:151-83; Wisdom G B., 1994. Methods Mol Biol. 32:433-40; Ishikawa E. et al., 1983. J Immunoassay 4:209-327; Oellerich M., 1980. J Clin Chem Clin Biochem. 18:197-208; Schuurs A H. and van Weemen B K., 1980. J Immunoassay 1:229-49).

The functional moiety may be attached to the antibody or antibody fragment in various ways, depending on the context, application and purpose.

A functional moiety may also be attached to the antibody or antibody fragment using standard chemical synthesis techniques widely practiced in the art [for example, refer to the extensive guidelines provided by The American Chemical Society (for example at: hypertexttransferprotocol:// worldwideweb (dot) chemistry (dot) org/portal/Chemistry)]. One of ordinary skill in the art, such as a chemist, will possess the required expertise for suitably practicing such chemical synthesis techniques.

Alternatively, a functional moiety may be attached to the antibody or antibody fragment by attaching an affinity tag-coupled antibody or antibody fragment of the invention to the functional moiety conjugated to a specific ligand of the affinity tag.

Various types of affinity tags may be employed to attach the antibody or antibody fragment to the functional moiety.

Examples of detectable moieties that can be used in the invention include but are not limited to radioactive isotopes, phosphorescent chemicals, chemiluminescent chemicals, fluorescent chemicals, enzymes, fluorescent polypeptides and epitope tags. The detectable moiety can be a member of a binding pair, which is identifiable via its interaction with an additional member of the binding pair, and a label which is directly visualized. In one example, the member of the binding pair is an antigen which is identified by a corresponding labeled antibody. In one example, the label is a fluorescent protein or an enzyme producing a colorimetric reaction.

When the detectable moiety is a polypeptide, the immunolabel (i.e. the antibody conjugated to the detectable moiety) may be produced by recombinant means or may be chemically synthesized by, for example, the stepwise addition of one or more amino acid residues in defined order using solid phase peptide synthetic techniques. Examples of polypeptide detectable moieties that can be linked to the antibodies of the invention using recombinant DNA technology include fluorescent polypeptides, phosphorescent polypeptides, enzymes and epitope tags.

Expression vectors can be designed to fuse proteins encoded by the heterologous nucleic acid insert to fluorescent polypeptides. For example, antibodies can be expressed from an expression vector fused with a green fluorescent protein (GFP)-like polypeptide. A wide variety of vectors are commercially available that fuse proteins encoded by heterologous nucleic acids to the green fluorescent protein from *Aequorea victoria* ("GFP"), the yellow fluorescent protein and the red fluorescent protein and their variants (e.g., Evrogen). In these systems, the fluorescent polypeptide is entirely encoded by its amino acid sequence and can fluoresce without requirement for cofactor or substrate. Expression vectors that can be employed to fuse proteins encoded by the heterologous nucleic acid insert to epitope tags are commercially available (e.g., BD Biosciences, Clontech).

Alternatively, chemical attachment of a detectable moiety to the antibodies of the invention can be effected using any suitable chemical linkage, direct or indirect, as via a peptide bond (when the detectable moiety is a polypeptide), or via covalent bonding to an intervening linker element, such as a linker peptide or other chemical moiety, such as an organic polymer. Such chimeric peptides may be linked via bonding at the carboxy (C) or amino (N) termini of the peptides, or via bonding to internal chemical groups such as straight, branched or cyclic side chains, internal carbon or nitrogen atoms, and the like. Such modified peptides can be easily identified and prepared by one of ordinary skill in the art, using well known methods of peptide synthesis and/or covalent linkage of peptides. Description of fluorescent labeling of antibodies is provided in details in U.S. Pat. Nos. 3,940,475, 4,289,747, and 4,376,110.

Exemplary methods for conjugating two peptide moieties are described herein below:

SPDP Conjugation:

Any SPDP conjugation method known to those skilled in the art can be used. For example, in one illustrative embodiment, a modification of the method of Cumber et al. (1985, Methods of Enzymology 112: 207-224) as described below, is used.

A peptide, such as an identifiable, (1.7 mg/ml) is mixed with a 10-fold excess of SPDP (50 mM in ethanol) and the antibody is mixed with a 25-fold excess of SPDP in 20 mM sodium phosphate, 0.10 M NaCl pH 7.2 and each of the reactions incubated, e.g., for 3 hours at room temperature. The reactions are then dialyzed against PBS.

The peptide is reduced, e.g., with 50 mM DTT for 1 hour at room temperature. The reduced peptide is desalted by equilibration on G-25 column (up to 5% sample/column volume) with 50 mM KH2PO4 pH 6.5. The reduced peptide is combined with the SPDP-antibody in a molar ratio of 1:10 antibody:peptide and incubated at 4° C. overnight to form a peptide-antibody conjugate.

Glutaraldehyde Conjugation:

Conjugation of a peptide (e.g., an identifiable) with an antibody can be accomplished by methods known to those skilled in the art using glutaraldehyde. For example, in one illustrative embodiment, the method of conjugation by G. T. Hermanson (1996, "Antibody Modification and Conjugation, in Bioconjugate Techniques, Academic Press, San Diego) described below, is used.

The antibody and the peptide (1.1 mg/ml) are mixed at a 10-fold excess with 0.05% glutaraldehyde in 0.1 M phosphate, 0.15 M NaCl pH 6.8, and allowed to react for 2 hours at room temperature. 0.01 M lysine can be added to block excess sites. After-the reaction, the excess glutaraldehyde is removed using a G-25 column equilibrated with PBS (10% v/v sample/column volumes).

Carbodiimide Conjugation:

Conjugation of a peptide with an antibody can be accomplished by methods known to those skilled in the art using a dehydrating agent such as a carbodiimide Most preferably the carbodiimide is used in the presence of 4-dimethyl aminopyridine. As is well known to those skilled in the art, carbodiimide conjugation can be used to form a covalent bond between a carboxyl group of peptide and an hydroxyl group of an antibody (resulting in the formation of an ester bond), or an amino group of an antibody (resulting in the formation of an amide bond) or a sulfhydryl group of an antibody (resulting in the formation of a thioester bond).

Likewise, carbodiimide coupling can be used to form analogous covalent bonds between a carbon group of an antibody and a hydroxyl, amino or sulfhydryl group of the peptide. See, generally, J. March, Advanced Organic Chemistry: Reaction's, Mechanism, and Structure, pp. 349-50 & 372-74 (3d ed.), 1985. By means of illustration, and not limitation, the peptide is conjugated to an antibody via a covalent bond using a carbodiimide, such as dicyclohexylcarbodiimide. See generally, the methods of conjugation by B. Neises et al. (1978, Angew Chem., Int. Ed. Engl. 17:522; A. Hassner et al. (1978, Tetrahedron Lett. 4475); E. P. Boden et al. (1986, J. Org. Chem. 50:2394) and L. J. Mathias (1979, Synthesis 561)).

Preferably, the affinity tag is a biotin molecule, more preferably a streptavidin molecule.

A biotin or streptavidin affinity tag can be used to optimally enable attachment of a streptavidin-conjugated or a biotin-conjugated functional moiety, respectively, to the antibody or antibody fragment due to the capability of streptavidin and biotin to bind to each other with the highest non covalent binding affinity (i.e., with a Kd of about $10^{-14}$ to $10^{-15}$). A biotin affinity tag may be highly advantageous for applications benefiting from. Thus, the antibody of invention can be a multimeric form of the antibody or antibody fragment, which may be optimally formed by conjugating multiple biotin-attached antibodies or antibody fragments of the invention to a streptavidin molecule, as described in further detail below.

Various methods, widely practiced in the art, may be employed to attach a streptavidin or biotin molecule to a molecule such as the antibody or antibody fragment to a functional moiety.

For example, a biotin molecule may be advantageously attached to an antibody or antibody fragment of the invention attached to a recognition sequence of a biotin protein ligase. Such a recognition sequence is a specific polypeptide sequence serving as a specific biotinylation substrate for the biotin protein ligase enzyme. Ample guidance for biotinylating a target polypeptide such as an antibody fragment using a recognition sequence of a biotin protein ligase, such as the recognition sequence of the biotin protein ligase BirA, is provided in the literature of the art (for example, refer to: Denkberg, G. et al., 2000. Eur. J. Immunol. 30:3522-3532). Preferably, such biotinylation of the antibody or antibody fragment is effected as described and illustrated in the Examples section below.

Alternately, various widely practiced methods may be employed to attach a streptavidin molecule to an antibody fragment, such as a single chain Fv (for example refer to Cloutier S M. et al., 2000. Molecular Immunology 37:1067-1077; Dubel S. et al., 1995. J Immunol Methods 178:201; Huston J S. et al., 1991. Methods in Enzymology 203:46; Kipriyanov S M. et al., 1995. Hum Antibodies Hybridomas 6:93; Kipriyanov S M. et al., 1996. Protein Engineering 9:203; Pearce L A. et al., 1997. Biochem Molec Biol Intl 42:1179-1188).

Functional moieties, such as fluorophores, conjugated to streptavidin are commercially available from essentially all major suppliers of immunofluorescence flow cytometry reagents (for example, Pharmingen or Becton-Dickinson). Standard recombinant DNA chemical techniques are preferably employed to produce a fusion protein comprising streptavidin fused to a polypeptidic functional moiety. Standard chemical synthesis techniques may also be employed to form the streptavidin-functional moiety conjugate. Extensive literature is available providing guidance for the expression, purification and uses of streptavidin or streptavidin-derived molecules (Wu S C. et al., 2002. Protein Expression and Purification 24:348-356; Gallizia A. et al., 1998. Protein Expression and Purification 14:192-196), fusion proteins comprising streptavidin or streptavidin-derived molecules (Sano T. and Cantor C R., 2000. Methods Enzymol. 326: 305-11), and modified streptavidin or streptavidin-derived molecules (see, for example: Sano T. et al., 1993. Journal of Biological Chemistry 270:28204-28209), including for streptavidin or streptavidin-derived molecules whose gene sequence has been optimized for expression in *E. coli* (Thompson L D. and Weber P C., 1993. Gene 136:243-6).

According to some embodiments of the invention, contacting the biological sample (e.g., the blood sample) with an anti-mortalin antibody is effected under conditions which allow immunocomplex formation. Such conditions may include buffers, temperature, salts, which increase the binding between the antibody to the antigen, yet avoids binding of the antibody to non-specific proteins or determinants, such as the vial, plate or vessel to which the antibody is added.

According to some embodiments of the invention, the anti-mortalin antibody is bound to a solid support.

According to some embodiments of the invention, the method further comprises determining a presence or level of the immunocomplex.

Methods of determining presence (or absence) of an immunocomplex and determining the presence and/or level of the antigen in a sample based on detection of the immunocomplex are known in the art, and include, for example, ELISA and Western blot analysis, radio immunoassay (RIA), Fluorescence activated cell sorting (FACS), surface plasmon resonance, immunohistochemistry, immunofluorescence, immunoprecipitation, nephelometry and the like.

Following is a non-limiting description of the immunological detection methods.

Enzyme linked immunosorbent assay (ELISA): This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Radio-immunoassay (RIA): In one version, this method involves precipitation of the desired protein (i.e., the substrate) with a specific antibody and radiolabeled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabeled antibody binding protein are employed. A sample containing an unknown amount of substrate is added in varying amounts. The decrease in precipitated counts from the labeled substrate is proportional to the amount of substrate in the added sample.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Immunohistochemical analysis: This method involves detection of a substrate in situ in fixed cells by substrate specific antibodies. The substrate specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxyline or Giemsa stain.

Nephelometry: This technique is used in medicine to quantify proteins based on antibody binding and measuring intensity of light scattering by the sample.

According to some embodiments of the invention, the immunocomplex is employed in an immunoprecipitation assay.

According to some embodiments of the invention, the immunoprecipitation assay is followed by mass spectroscopy or nephelometry.

According to some embodiments of the invention, the immunological method uses an anti-mortalin antibody (or antibodies) which are conjugated to a surface plasmon resonance. The anti-mortalin antibody, coated to the surface of the chip, captures mortalin, and the response elicited by the binding is detected.

According to some embodiments of the invention, the level of the immunocomplex is determined by an Enzyme-linked immunosorbent assay (ELISA).

According to some embodiments, the immunological method is followed by mass spectroscopy analysis of the immuno-precipitant. For example, the immuno-precipitant can be dissociated with an enzyme (e.g., trypsin) and be subject to mass spectroscopy using known parameters.

According to some embodiments, the level of immunocomplex is compared to a control or reference sample (e.g., from a healthy subject, devoid of the cancer).

According to some embodiments of the invention, the reference sample is obtained from a subject of the same species e.g. human.

According to some embodiments of the invention, the control or reference sample is obtained from a healthy subject (e.g., devoid of the cancer) matched with the same ethnic group, age, sex, and/or body mass index (BMI).

According to some embodiments of the invention, the control or reference sample is of the same type as the biological sample (e.g., body fluid) from the subject in need of diagnosis. For example, if the biological sample of the subject is a serum sample, then, the control or reference sample is also a serum sample.

According to some embodiments, the level of immunocomplex is compared to a calibration curve or calibration database obtained using known amounts of mortalin such as that produced by the present inventors and shown in FIG. 1 and described in Example 1 of the Examples section which follows.

Thus, the methods described herein can be used to determine the presence and/or level of soluble mortalin in a sample of the subject and can then be compared to the level in a reference sample.

As described above and in the Examples section which follows, the present inventors have uncovered, for the first time, that the level of mortalin in a blood sample of a subject having a solid tumor such as colorectal cancer can be used as a powerful predictor for the prognosis of the subject having the cancer.

Thus, according to an aspect of some embodiments of the invention, there is provided a method of predicting prognosis of a subject diagnosed with a solid cancerous tumor, the method is effected by determining a level of soluble mortalin according to the method of some embodiments of the invention, wherein (i) when a level of the soluble mortalin is above a pre-determined threshold, then the subject is predicted to have poor prognosis as compared to an expected prognosis based on the subject's tumor's stage, age and/or gender; and (ii) when a level of the soluble mortalin is below a pre-determined threshold, then the subject has good prognosis as compared to an expected prognosis based on the subject's tumor's stage, age and/or gender.

As used herein the phrase "predicting prognosis" refers to determining the likelihood of a subject diagnosed with the cancer to have good or poor prognosis as compared to the expected prognosis based the subject's tumor's stage, age and/or gender.

It should be noted that the prognosis of a subject diagnosed with a disease such as cancer is currently determined based on known measurements, known as the gold standard. For example, tumor stage can be determined using criteria which are based on histological evaluation of the tumor (e.g., by a Pathologist), presence or absence of metastases, invasion into healthy nearby tumor, metastases in lymph nodes or distance metastases.

According to some embodiments of the invention, the tumor stage is determined by Classification of Malignant Tumours (TNM) criteria.

According to some embodiments of the invention, TNM is TNM-T based on tumor size and state of invasion to nearby tissue.

According to some embodiments of the invention, TNM is TNM-N based on extent of lymph node involvement.

According to some embodiments of the invention, TNM is TNM-M based on presence or absence of distant metastases.

According to some embodiments of the invention, the prognosis refers to the survival period of the subject having the solid tumor.

According to some embodiments of the invention, the survival period of the subject having the solid tumor is from the time of diagnosing the cancer until death occurs.

According to some embodiments of the invention, the method of determining the prognosis of the subject is performed shortly after diagnosing the cancer in the subject.

According to some embodiments of the invention, the method of determining the prognosis of the subject is performed within a few days (e.g., 1-30 days), a few weeks (e.g., 2-10 weeks) or a few months (e.g., within 1-12 months) from the date of diagnosing the cancer in the subject.

For example, as described in the Examples section which follows, testing the level of mortalin in the blood sample of the colorectal cancer patients was performed within 4-6 weeks after surgery when the patients came for a routine follow up at the clinic.

According to some embodiments of the invention, a good prognosis refers to better health condition and/or longer survival time (in months or years) as compared to the expected prognosis of the subject as determined using the gold standard parameters.

According to some embodiments of the invention, when the solid tumor is colorectal cancer, then a good prognosis is characterized by about 72 months mean survival time.

According to some embodiments of the invention, a poor prognosis refers to worse health condition and/or shorter survival time (in months or years) as compared to the expected prognosis of the subject as determined using the gold standard parameters.

According to some embodiments of the invention, when the solid tumor is colorectal cancer, then a poor prognosis is characterized by about 43 months mean survival time.

According to some embodiments of the invention, the level of mortalin in a blood sample of a subject having colorectal cancer is between about 5-300 nanogram per milliliter (ng/ml), e.g., between about 8-250 ng/ml, e.g., between about 10-214 ng/ml.

According to some embodiments of the invention, the level of the mortalin immunocomplex in a biological sample (e.g., body fluid, e.g., serum) is between about 10 nanogram per milliliter (ng/ml) to about 214 ng/ml.

According to some embodiments of the invention, the level of the mortalin in a blood sample of a control, healthy subject (e.g., devoid of the cancer), is apparently 0 ng/ml.

As used herein the phrase "pre-determined threshold" refers to level of mortalin [e.g., concentration of mortalin in a biological sample (e.g., body fluid) which can be measured in nanogram per milliliter; or in molar units (e.g., milimolar or molar)] which discriminates between subjects diagnosed with the cancer and having a good prognosis and subjects diagnosed with the cancer and having a poor prognosis.

As described in the Examples section which follows, the predetermined threshold can be determined retrospectively using archive samples with a known clinical outcome, e.g., a known survival period. Tools for determining such a threshold which discriminates between the two groups of patients, e.g., those having good prognosis from those having poor prognosis, are known in the art, and include, for example, the receiver operating characteristic (ROC) calculation which yields optimal stratification of patients regarding mortalin levels and survival (Example 2 of the Examples section which follows).

Once determined, the threshold of mortalin concentration in the body fluid of the subject can be used to predict the prognosis of a subject having the solid tumor.

For example, as shown in Example 2 below, the predetermined threshold of 60 ng/ml of mortalin in the serum was found to accurately discriminate between patients with colorectal cancer and having a poor prognosis (e.g., having a concentration of mortalin which is equal to or higher than 60 ng/ml) or a good prognosis (e.g., having a concentration of mortalin which is lower than 60 ng/ml).

According to some embodiments of the invention, the predetermined threshold is about 60 ng/ml of mortalin in the biological sample (e.g., body fluid).

According to some embodiments of the invention, the level of mortalin in the biological sample (e.g., body fluid, e.g., blood) enables the classification of a subject as having good or poor prognosis (e.g., long or short survival periods).

According to some embodiments of the invention, the method further comprising: classifying the subject as having good or poor prognosis based on the level of the soluble mortalin, thereby predicting the prognosis of the subject diagnosed with the cancer.

As used herein the term "diagnosing" refers to determining presence or absence of a pathology (e.g., a disease, disorder, condition or syndrome), classifying a pathology or a symptom, determining a severity of the pathology, monitoring pathology progression, forecasting an outcome of a pathology and/or prospects of recovery and screening of a subject for a specific disease.

According to some embodiments of the invention, screening of the subject for a specific disease is followed by substantiation of the screen results using gold standard methods.

As shown in Tables 4 and 5 and Example 3 of the Examples section which follows, determining the level of mortalin along with the level of sHSP70 results in an even higher predicting power for prognosis of colorectal cancer patients.

Thus, according to some embodiments of the invention, the method further comprising:

(a) determining the level of soluble heat shock protein 70 (sHSP70) in the sample, wherein when a level of the soluble mortalin and the sHSP70, each is above a predetermined threshold in the biological sample (e.g., blood sample), then the subject is predicted to have a poor prognosis as compared to an expected prognosis based the subject's tumor's stage, age and/or gender; and (b) classifying the subject as having good or poor prognosis based on the mortalin and the sHSP70 levels in the biological sample (e.g., body fluid), thereby predicting the prognosis of the subject diagnosed with the solid tumor.

As used herein the soluble heat shock protein 70 (sHSP70) refers to a 70 kDa protein present in the cytosol of the cell.

Non-limiting examples of cytosolic HSP70 protein which can be identified in the biological sample (e.g., blood sample) according to the method or kit of some embodiments of the invention include HSPA1A (GenBank Accession No. NP_005336.3; SEQ ID NO:3), HSPA1B (GenBank Accession No. NP_005337.2; SEQ ID NO:4), HSPA2 (GenBank Accession No. NP_068814.2; SEQ ID NO:5), HSPA1L (GenBank Accession No. NP_005518.3; SEQ ID NO:6), HSPA6 (GenBank Accession No. NP_002146.2; SEQ ID NO:7) and HSPA8 (GenBank Accession Nos. NP_006588.1 and NP_694881; SEQ ID NOs:8 and 9).

According to some embodiments of the invention, the cytosolic (soluble) HSP70 which is identified by the method or kit of the invention is HSPA1A.

Antibodies directed against soluble HSP70 are available from various commercial suppliers such as R&D systems [e.g., an ELISA kit, DYC1663E, Human/Mouse/Rat Total HSP70/HSPA1A DuoSet IC Econ Pk, 15 Plt].

According to some embodiments of the invention, the predetermined level of sHSP70 is 1.67 ng/ml in a body fluid of a subject such as a serum sample.

According to some embodiments of the invention, the method further comprising informing the subject of the predicted prognosis (i.e., good or poor prognosis) as compared to the expected prognosis based on the gold standard criteria for determining prognosis of the subject having the solid tumor, e.g., as predicted based on tumor's stage, subject's age and/or subject's gender (i.e., male or female).

As used herein the phrase "informing the subject" refers to advising the subject on the predicted prognosis based on the level of mortalin or the level of mortalin and sHSP70 in the biological sample (e.g., body fluid) of the subject (e.g., in the blood sample).

Once the predicted prognosis is determined, the results can be recorded in the subject's medical file, which may assist in selecting a treatment regimen for the subject.

The agents of some embodiments of the invention which are described hereinabove for determining the presence and/or level of mortalin and/or sHSP70 may be included in a diagnostic kit/article of manufacture preferably along with appropriate instructions for use and labels indicating FDA approval for use in determining the presence and/or level of mortalin in a blood sample and/or predicting prognosis of a subject diagnosed with cancer.

Such a kit can include, for example, at least one container including at least one of the above described diagnostic agents (e.g., anti-mortalin antibody, and/or anti soluble HSP70 antibody) and an imaging reagent packed in another container (e.g., enzymes, secondary antibodies, buffers, chromogenic substrates, fluorogenic material). The kit may also include appropriate buffers and preservatives for improving the shelf-life of the kit.

According to an aspect some embodiments of the invention, there is provided a kit which comprises at least two distinct antibodies to mortalin directed against different epitopes of the mortalin.

According to an aspect some embodiments of the invention, the kit is for determining presence and/or level of soluble mortalin in a biological sample (e.g., body fluid) and/or predicting prognosis of a subject diagnosed with solid tumor.

According to an aspect some embodiments of the invention, the kit includes instructions for use in determining presence and/or level of soluble mortalin in a biological sample (e.g., body fluid) and/or predicting prognosis of a subject diagnosed with solid tumor.

According to some embodiments of the invention, one antibody of the at least two antibodies is a mouse monoclonal against human mortalin.

According to some embodiments of the invention, one antibody of the at least two antibodies is a goat polyclonal against human mortalin.

According to some embodiments of the invention, the mouse monoclonal antibody against human mortalin is attached to a solid support.

According to some embodiments of the invention, the kit further comprising a secondary antibody for binding one of the at least two antibodies.

According to some embodiments of the invention, the kit further comprising an Enzyme-linked immunosorbent assay (ELISA) plate.

According to some embodiments of the invention, the kit further comprising an anti-soluble heat shock protein 70 (sHSP70) antibody.

According to some embodiments of the invention, the kit further comprising a reference sample. For example, the kit may comprise a biological sample such as blood which is obtained from a healthy subject, or from a subject diagnosed with cancer and having a known clinical outcome, e.g., prognosis, e.g., known survival period.

According to some embodiments of the invention, the kit further comprises a calibration standard for mortalin levels, e.g., with serial dilutions of known concentrations of mortalin. The calibration standard can be in a solid or liquid form (e.g., solution), and can be also attached to a solid surface. According to some embodiments of the invention, the calibration standard has mortalin diluted in normal serum, or in a biological sample (e.g., body fluid) of a normal (healthy, control) subject.

According to some embodiments of the invention, the kit further comprises a calibration standard for sHSP70 levels, e.g., with serial dilutions of known concentrations of sHSP70. The calibration standard can be in a solid or liquid form (e.g., solution), and can be also attached to a solid surface. According to some embodiments of the invention, the calibration standard has sHSP70 diluted in normal serum, or in a biological sample (e.g., body fluid) of a normal (healthy, control) subject.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed.

(1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Serum samples—Serum samples of colorectal cancer patients were collected at the outpatient oncology clinic of the 3rd Department of Internal Medicine, Semmelweis University, Budapest. A number of 175 consecutive patients, diagnosed with colorectal cancer, who were willing to give informed consent for the study, were enrolled regardless of tumor stage. Serum samples of 121 of these patients were available for this study and the median follow-up time was increased from 33 to 42 months. This patient cohort was already tested for the association between sHsp70 levels and survival (20) and between acute phase proteins plus sHsp70 and survival (21), except for four patients with no available serum samples for the present study. In the majority of cases, the primary tumor was removed surgically, according to relevant international guidelines, and patients were enrolled 4-6 weeks after surgery when blood was collected for the current study. In 16 cases, the primary tumor could not be removed before inclusion; these patients had advanced, metastatic tumors and were referred for primary chemotherapy. The patients were followed during and after chemotherapy in a protocol-based manner and health status and disease outcome were registered. More information on the patients is available in earlier publications (20, 21). The study received approvals by the ethical committees of Semmelweis University, Budapest and Tel Aviv University, Tel Aviv. 163 of the 175 patients were followed up and their survival recorded.

Mortalin EUSA —To be able to measure serum levels of Mortalin the present inventors developed the following capture enzyme-linked immunosorbent assay (ELISA). Wells of 96 well MaxiSorp Nunc-Immuno plate (Thermo Fisher Scientific, Rochester, N.Y.) were coated overnight at 4° C. with 1 mg/ml mouse monoclonal antibody directed to human mortalin (StressMarq Biosciences Inc., Victoria, Canada) in TB buffer (50 mM Tris Base pH 7.0, 100 mM NaCl). The wells were blocked with bovine serum albumin 15 mg/ml (Sigma-Aldrich, Rehovot, Israel) in TBS (Tris-buffered saline) for 1 hour at 37° C. and then serum samples diluted 1:3 in TB were added to the wells for 2 hours at 37° C., Next, the wells were washed with TBT (TB with 0.05% TWEEN®-20 (Croda International PLC. Polyoxyethylene-sorbitan monolaurate) and treated with a goat anti-human mortalin polyclonal antibody (Santa Cruz Biotechnology, Santa Cruz, Calif.) diluted in TB for 1 hour at 37° C. Finally, after a wash with TBT. peroxidase-conjugated donkey anti-goat IgG (Jackson ImmunoResearch Laboratories, West Grove, Pa.) diluted in TB was added for 1. hour at 25° C. Antibody binding was quantified by using TMB One Component Microwell Substrate (Southern Biotech, Birmingham, Ala.) and absorbance was read at 450 nm in a Microplate Reader (Spectrafluor plus, Tecan, Austria). Calibration of the quantity of mortalin was included in each ELISA plate with 0-2.5 ng purified recombinant mortalin mixed with normal human serum (same dilution as the tested samples). Specificity of the anti-mortalin antibodies used was confirmed in Western Blots showing a single protein band in whole cell lysates [similar to the bands shown in (17)]. Purity of the recombinant mortalin was also confirmed (17). Absorbance of normal serum without recombinant mortalin was subtracted from all samples in the plate. A typical calibration curve is shown in FIG. 1.

Statistical analysis—Statistical analysis was performed using the SPSS 15.0 software (SPSS Inc., Chicago, Ill.). Patients' survival was tested by the Kaplan-Meier survival analysis, using the Log Rank test. The power of the study to identify the observed difference in mortality rate (0.18) between low- and high-mortalin groups was 0.78. The impact of soluble mortalin and other factors on patients' survival was tested by the Cox Proportional hazards analysis (univariate and multivariate analyses). The results of the Cox regression models are presented as hazard ratios, the corresponding 95% confidence intervals (CI) and the Wald chi-square and p values of likelihood ratio tests.

Example 1

Figure 3:
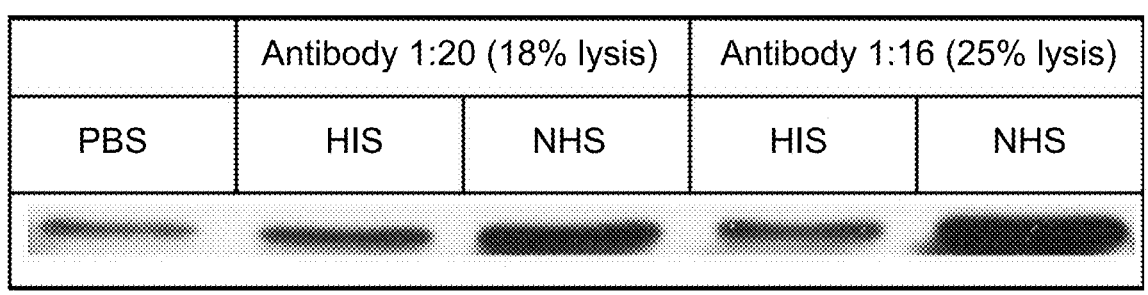
FIG. 3 is a Western blot analysis depicting release of mortalin from HCT116 colon carcinoma cells. HCT116 cells ($2.5 \times 10^6$) were treated for 30 minutes on ice with diluted (1:16 or 1:20) rabbit anti-human cancer cells antiserum (prepared by the present inventors). Then, normal human serum (NHS) or heat-inactivated serum (HIS) (50% final concentration) was added as a source of complement and control, respectively. After 10 minutes of incubation at 37° C., the cells were washed and suspended in Hank's Balanced Salt Solution (HBSS) buffer. After 10 minutes incubation at 37° C., the cells were removed by centrifugation and the supernatant was further subjected to centrifugation for 15 minutes at 5,000 g at 4° C. The final supernatant was subjected to SDS-PAGE and Western Blotting with mouse anti-mortalin mAb and a secondary peroxidase-conjugated goat anti-mouse IgG antibody. The extracellular mortalin bands are shown. Cells were also treated with the antibody and complement for 60 minutes at 37° C. to ensure that the conditions are indeed sublytic (lysis percentages shown in parentheses). Basal mortalin release is shown with cells incubated with PBS alone. As shown, NHS induces release of mortalin more than HIS.

Development of a Sensitive ELISA for Determining Mortalin Levels in a Blood Sample Experimental Results Mortalin is shed in vitro from complement attacked viable human erythroleukemia cells (16). Release of mortalin in vitro was also demonstrated from human colon carcinoma HCT116 cells (FIG. 3), mouse colorectal CT26 cells, mouse lymphoma EL4 cells, mouse bladder carcinoma MBT2 cells and human B lymphoma Raji cells (data not shown).

Calibration of the mortalin ELISA assay for quantitation of mortalin concentrations in a biological sample—In order to measure mortalin level in patients' blood, the present inventors have developed a sensitive mortalin ELISA with a low background reading. Several alternative protocols were tested and finally the captured ELISA described in details under the "General Materials and Experimental Methods" section above was found to be satisfactory. This mortalin ELISA gave a reproducible and sensitive detection of 0.25 ng of mortalin in human serum diluted 3 folds. Each ELISA plate had wells with normal human serum alone or human serum with increasing amounts of recombinant mortalin. Normal human serum gave a low background readout to that was subtracted from all samples. The recombinant mortalin samples gave a linear dose-dependent calibration curve (FIG. 1) that was used to convert the optical density readout of the clinical samples into nanogram (ng) of mortalin per sample.

Example 2

Determination of Mortalin Levels in Serum of Patients with Colorectal Cancer

Experimental Results

Determination of the concentration of mortalin in sera of patients with colorectal cancer—By using this ELISA, significant amounts of soluble mortalin were detected in the serum samples of all colorectal cancer patients (14-215 ng/ml). The patients were divided into two groups, according to their serum mortalin level. The low mortalin group (n=88) had serum mortalin concentration below 60 ng/ml, whereas the high mortalin group (n=33) had levels equal to or higher than 60 ng/ml (60 ng/ml). This concentration of mortalin (60 ng/ml) was chosen based on Receiver operating characteristic (ROC) calculation to yield optimal stratification of patients regarding mortalin levels and survival.

Correlation between mortalin levels and other tumor determinants—Mortalin concentrations were analyzed in relation to the tumor stage of the patients determined in earlier studies (20, 21). There was no difference in the mortalin levels among the patients with different size of tumors (TNM-T) (p=0.151, Kruskal-Wallis test), among patients with different extent of lymph node involvement (TNM-N) (p=0.346, Kruskal-Wallis test) or between patients with or without distant metastases (TNM-M) (p=0.205, Mann-Whitney test). Likewise, there was no significant association between mortalin levels and different Duke's grade categories and grade of primary tumor (both p>0.050, data not shown). Similarly, data was available on the serum levels of sHSP70, C-reactive protein (CRP) and C1-Inhibitor in these patients (20, 21). Mortalin concentrations did not show correlation to the sHSP70 concentrations (Spearman correlation coefficient R=0.051, p=0.580) or CRP levels (R=0.018, p=0.878) whereas a significant correlation (R=0.335, p<0.001) was found between serum mortalin and C1-Inhibitor concentrations (28).

Example 3

Mortalin as a Predictor of Colorectal Prognosis and Patient's Survival

Experimental Results

Univariate survival analysis revealed mortalin as a predictor for patient's survival—Kaplan-Meier survival analysis of patients with low (<60 ng/ml) versus (vs.) high (≥60 ng/ml) mortalin level in serum during a 10 year follow-up gave a Log Rank overall comparison of P=0.042 between the two groups, with 113 months estimated median survival in the low mortalin group and 29 months median survival in the high mortalin group (FIG. 2 and Table 1 below). Univariate analysis by Cox regression of the variables: age and sex of the patients, TNM-N and TNM-M stage of the disease as well as serum mortalin and sHsp70 concentrations are presented in Table 2 below. Only patients without missing data were included in this analysis (n=99). Age was found to be a highly significant factor with a hazard of 1.04 per year (P=0.002). Females had a Hazard of 1.62 (P=0.029) relative to males. Both TNM-N (metastases in the regional lymph node) and TNM-M (distant metastases) were highly significant predictors of mortality while TNM-T was not (data not shown). High sHSP70 serum concentration (>1.65 ng/ml) was associated with mortality with a hazard ratio (HR) of 1.86 (p=0.006). High mortalin (≥60 ng/ml) level is a significant factor (P=0.048) with a hazard ratio of 1.73. In this analysis, patients with high and low serum mortalin levels had a mean survival time of 43.19 (32.39-53.99) months and 72.52 months (62.78-82.76), respectively (p=0.046).

TABLE 1

Provided are the survival data of patients at risk with low or high mortalin. Data is also presented in FIG. 2.

| Mortalin | Patients at risk (0-60 months) | | | | | |
|---|---|---|---|---|---|---|
| Low | 89 | 80 | 70 | 56 | 50 | 47 |
| High | 33 | 29 | 22 | 13 | 12 | 12 |

TABLE 2

Univariate Cox-regression analysis of the association between age, sex of the colorectal cancer patients, TNM staging, as well as sHsp70 or mortalin serum levels and their survival.

| Variable* | Significance (P) | Hazard Ratio | 95.0% confidence interval | |
|---|---|---|---|---|
| | | | Lower | Upper |
| Age at diagnosis | 0.002 | 1.041 | 1.015 | 1.068 |
| Sex | 0.029 | 1.620 | 1.049 | 2.500 |
| TNM-N | 0.001 | 3.211 | 1.654 | 6.231 |
| TNM-M | <0.001 | 3.346 | 1.925 | 5.815 |
| sHsp70 | 0.006 | 1.858 | 1.190 | 2.901 |
| Mortalin | 0.048 | 1.729 | 1.004 | 2.946 |

*Age (years); Sex (female/male); TMN-N (1 or 2 metastasis in the regional lymph nodes vs. 0, yes/no); TNM-M (distant metastasis, yes/no); sHSP70 (high: >median 1.67 ng/ml, low: <1.67 ng/ml); Mortalin (high: >median, 60 ng/ml, low: <60 ng/ml).

Multivariate analysis: Independent and additive effects of risk factors—The association of the same variables with mortality of the cancer patients was evaluated by multivariate Cox regression analysis (Table 3, below). The effects of age and sex were found to be insignificant, while the hazard of TNM-N1+TNM-N2 stages vs. TNM-N0 stage (lymph nodes involved, yes vs. no) remained highly significant (HR 3.34 (p=0.001). Similarly, patients with distant metastasis had significantly higher risk (HR: 4.04; p<0.001) than those with no distant metastases. In the multivariable model, the hazard ratio associated with high sHsp70 was 3.508 (p<0.001) while high mortalin concentrations exhibited a weaker but still significant association with the mortality of patients independently of the sHSP70 levels (Table 3, below).

TABLE 3

Multivariate analysis by Cox-regression of the association between age, and sex of the patients as well as high baseline sHsp70 levels and high baseline mortalin levels on survival of the patients with colorectal cancer.

| Variable* | Significance (P) | Hazard Ratio | 95.0% confidence interval | |
|---|---|---|---|---|
| | | | Lower | Upper |
| Age at diagnosis | 0.488 | 1.013 | 0.977 | 1.050 |
| Sex | 0.900 | 0.959 | 0.497 | 1.850 |
| TNM-N | 0.001 | 3.337 | 1.661 | 6.704 |
| TNM-M | <0.001 | 4.044 | 2.014 | 8.118 |
| mortalin | 0.044 | 1.976 | 1.019 | 3.831 |
| sHsp70 | <0.001 | 3.508 | 1.753 | 7.019 |

*Age (years); Sex (female/male); TMN-N (1 or 2 metastasis in the regional lymph nodes vs. 0, yes/no); TNM-M (distant metastasis, yes/no); sHSP70 high: >median 1.67 ng/ml, low: <1.67 ng/ml); Mortalin (high: >median, 60 ng/ml, low: <60 ng/ml).

Thereafter the present inventors analyzed the survival of the patients stratified according to sHSP70 and mortalin levels (FIG. 4 and Table 4 below). In this type of multivariate analysis, high mortalin level with low sHsp70 or low mortalin with high sHsp70 did not affect the mortality of patients. In contrast, patients with concomitant high mortalin and high sHSP70 concentrations had a 4.2 times higher hazard of mortality than patients with both low sHSP70 and low mortalin levels, indicating the additive nature of these two biomarkers (FIG. 4). Median survival time of the patients with high mortalin/high sHSP70 and low mortalin/low sHSP70 levels were 27.5 (13.3-34.3) months and 57.0 (31.0-81.0) months, respectively. In addition, the mean survival time (from FIG. 4) of patients with high mortalin and high sHsp70 was: 24.9+/−14.0 months and that of patients with low mortalin and low sHsp70: 54.6+/−30.8 months.

TABLE 4

Provided are the survival data of patients at risk with low or high mortalin and Hsp70. Data is also presented in FIG. 4.

| Mortalin/Hsp70 | Patients at risk (0-60 months) | | | | |
|---|---|---|---|---|---|
| Low/Low | 46 | 43 | 39 | 35 | 33 | 32 |
| High/Low | 43 | 40 | 35 | 31 | 29 | 28 |
| Low/High | 14 | 12 | 10 | 8 | 7 | 6 |
| High/High | 18 | 14 | 8 | 5 | 3 | 3 |

Finally, the present inventors examined the additive impact of serum concentrations of mortalin and sHSP70 on prediction of patients' survival, as compared to the baseline model that includes the basic demographic variables as well as the tumor stage (Table 5, below). According to the results of the likelihood-ratio test ($\chi^2=26.846$, p<0.001), addition of the biomarkers sHsp70 and mortalin to the baseline model significantly increased the survival-predicting value of the model. In the subgroup of patients with concomitantly high sHsp70 and mortalin levels, a hazard rate of 8.176 (95% CI 3.267-20.463, P<0.001) was observed, indicating that the baseline model (clinical stage, age and sex) and the biomarkers are independent and additive predictors of mortality in colorectal cancer. An attempt to include serum levels of CRP in the model did not result in an increase in the strength of association with the survival of the patients (data not shown).

TABLE 5

Additive effect of the high mortalin and high sHSP70 levels in serum on the age and tumor TNM-dependent mortality risk of patients with colorectal cancer. Analysis by model-building tool of Cox regression analysis.

| Variable* | Significance (P) | Hazard Ratio | 95.0% confidence interval | |
|---|---|---|---|---|
| | | | Lower | Upper |
| Model 1 | | | | |
| Age at diagnosis | 0.098 | 1.030 | 0.995 | 1.066 |
| Sex | 0.865 | 0.947 | 0.508 | 1.768 |
| TNM-N | 0.003 | 1.853 | 1.234 | 2.784 |
| TNM-M | 0.001 | 3.130 | 1.630 | 6.013 |
| Model 2 | | | | |
| Age | 0.323 | 1.017 | 0.983 | 1.052 |
| Sex | 0.571 | 1.218 | 0.617 | 2.404 |
| TNM-N | 0.003 | 1.879 | 1.244 | 2.840 |
| TNM-M | <0.0001 | 5.000 | 2.423 | 10.318 |
| Mortalin low & sHSP70 low | — | — | — | — |
| Mortalin high & sHSP70 low | 0.223 | 0.390 | 0.086 | 1.772 |
| Mortalin low & sHSP70 high | 0.123 | 1.836 | 0.849 | 3.974 |
| Mortalin high & sHSP70 high | <0.001 | 8.176 | 3.267 | 20.463 |

Likelihood-ratio-test as compared to model 1: $\chi^2 = 26.846$. p < 0.0001
*Age (years); Sex (female/male); TMN-N (1 or 2 metastasis in the regional lymph nodes vs. 0, yes/no); TNM-M (distant metastasis, yes/no); sHSP70 (high: >median 1.67 ng/ml, low: <1.67 ng/ml); Mortalin (high: >median, 60 ng/ml, low: <60 ng/ml). Number of patients in the different (mortalin/sHsp70): low/low-46; high/low-43; low/high-14; high/high-18.

Analysis and Discussion

As shown here, colorectal cancer patients have elevated mortalin concentrations in their blood serum. This finding is surprising since mortalin is a mitochondrial protein and expected to be intracellular and not extracellular. Based on the in vitro study that demonstrated secretion of mortalin from cancer cells during an immune attack (16), the present inventors have hypothesized that such a release of mortalin may occur also in vivo during an immune attack. However, finding of circulating mortalin in the absence of any therapy was surprising and unexpected.

Development of a novel and sensitive mortalin ELISA permitted the present inventors to quantify the soluble mortalin level in blood serum of colorectal cancer patients. The amount of circulating soluble mortalin was found to be highly variable (10-214 ng/ml) and was independent on the stage of the disease. This study raises additional intriguing questions regarding the function of extracellular mortalin, release of mortalin in other cancers and, in general, in disease, and the effect of therapy on serum mortalin levels. Here, the present inventors correlated the amount of circulating mortalin with survival of the cancer patients.

The cohort of cancer patients studied here was part of a larger group of 175 colorectal cancer patients studied earlier in which the level of soluble cytosolic Hsp70 was analyzed. Correlation was found between high sHSP70 and faster disease progression in colorectal cancer (20). A follow up study examined in the same patients several other potential prognostic bio-markers (21). High (above median) levels of CRP, C1-INH and sHSP70 were found to be independently associated with poor patient survival. The additive effect of high sHSP70, CRP and C1-INH levels on the survival of patients exceeded that of high sHSP70 alone (21). Updated survival information since the previous study was available on 163 patients. Serum sample of 121 patients were tested for soluble mortalin levels. Patients that exhibited a higher mortalin level (>60 ng/ml) also exhibited a significantly shorter median survival time (29 months) than patients that exhibited low mortalin level (113 months, P=0.042). The hazard value of high mortalin is 1.730. Therefore, without being bound by any theory, high circulating mortalin level is proposed as a risk factor in colorectal carcinoma. Multivariate analysis of survival data of 99 patients, for which age, sex, cancer stage, soluble HSP70 and mortalin information was available, indicated that patients with both high soluble HSP70 and high mortalin had more than 8-times higher risk of mortality (8.176, 3.267-20.463, P<0.001) as compared to those with low concentrations of both biomarkers. Without being bound by any theory, it is concluded that having concomitant high circulating HSP70 and mortalin levels indicates bad prognosis in colorectal cancer patients, thus measurement of these two biomarkers may be informative in this setting.

Immunohistochemical analysis demonstrated that mortalin is over-expressed in several tumor types, including colorectal adenocarcinoma and hepatocellular carcinoma (11, 14, 15, 22). Elevated mortalin in liver cancer was associated with metastasis and early cancer recurrence (22). Over-expression of mortalin in colorectal adenocarcinomas is also correlated with poor survival (15). Apparently, mortalin confers an advantage to cancer growth and metastasis, but the mechanism is still poorly characterized. In addition, mortalin promotes cell resistance to complement-dependent cytotoxicity (CDC) and may permit escape of cancer cells from antibody-based immunotherapy (16-18). Down regulation of mortalin, using siRNA, antibodies or MKT-077 enhance cells sensitivity to CDC, whereas over-expression of mortalin enhanced cell resistance to CDC (Pilzer et al. 2010, Int. J. Cancer 126:1428-1435). As shown here, serum levels of mortalin and HSP70 and the TNM stage are apparently independent determinants in survival of colorectal cancer patients. Without being bound by any theory, this may suggest that mortalin and HSP70 are secreted into the blood from different tissues and/or under distinct signals. The trigger that has induced in these patients mortalin release into the blood and the origin of this mortalin remain to be identified. Without being bound by any theory, it is possible that inflammatory or other stress responses cause secretion of mortalin into the circulation from metastatic cells and/or non-cancerous affected tissues.

Cytosolic Hsp70 is also elevated in hepatocellular carcinoma compared with noncancerous liver tissue (23, 24). Expression level of Hsp70 in bladder cancer was significantly correlated with major prognostic indicators, including pathologic stage and tumor grade. Treatment of the bladder cancer cells with siRNA directed to Hsp70 sensitizes them to chemotherapy (25).

Extracellular Hsp70 was released from healthy cells (26) and was found in serum of normal individuals (27). Without being bound by any theory, the fact that they are both independent on tumor stage may propose that the main source for the two proteins in blood may not be the cancer cells themselves. Alternatively, it is possible that mortalin and Hsp70 are released to a similar extent from early stage and more advanced cancer cells but under distinct signals and are each associated with a more aggressive cancer phenotype.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

ADDITIONAL REFERENCES ARE CITED IN TEXT

1. Kang, P. J., J. Ostermann, J. Shilling, W. Neupert, E. A. Craig, and N. Pfanner. 1990. Requirement for hsp70 in the mitochondrial matrix for translocation and folding of precursor proteins. *Nature* 348:137-143.
2. Wiedemann, N., A. E. Frazier, and N. Pfanner. 2004. The protein import machinery of mitochondria. *The Journal of biological chemistry* 279:14473-14476.
3. Merrick, B. A., V. R. Walker, C. He, R. M. Patterson, and J. K. Selkirk. 1997. Induction of novel Grp75 isoforms by 2-deoxyglucose in human and murine fibroblasts. *Cancer Lett* 119:185-190.
4. Sadekova, S., S. Lehnert, and T. Y. Chow. 1997. Induction of PBP74/mortalin/Grp75, a member of the hsp70 family, by low doses of ionizing radiation: a possible role in induced radioresistance. *Int J Radiat Biol* 72:653-660.
5. Massa, S. M., F. M. Longo, J. Zuo, S. Wang, J. Chen, and F. R. Sharp. 1995. Cloning of rat grp75, an hsp70-family member, and its expression in normal and ischemic brain. *J Neurosci Res* 40:807-819.
6. Tsuchiya, T., J. M. Dhahbi, X. Cui, P. L. Mote, A. Bartke, and S. R. Spindler. 2004. Additive regulation of hepatic gene expression by dwarfism and caloric restriction. *Physiol Genomics* 17:307-315.
7. Craig, E. A., J. Kramer, and J. Kosic-Smithers. 1987. SSC1, a member of the 70-kDa heat shock protein multigene family of *Saccharomyces cerevisiae*, is essential for growth. *Proc Natl Acad Sci USA* 84:4156-4160.
8. Liu, Y., W. Liu, X. D. Song, and J. Zuo. 2005. Effect of GRP75/mthsp70/PBP74/mortalin overexpression on intracellular ATP level, mitochondrial membrane potential and ROS accumulation following glucose deprivation in PC12 cells. *Mol Cell Biochem* 268:45-51.
9. Taurin, S., V. Seyrantepe, S. N. Orlov, T. L. Tremblay, P. Thibault, M. R. Bennett, P. Hamet, and A. V. Pshezhetsky. 2002. Proteome analysis and functional expression identify mortalin as an antiapoptotic gene induced by elevation of [Na+]i/[K+]i ratio in cultured vascular smooth muscle cells. *Circ Res* 91:915-922.
10. Xu, L., L. A. Voloboueva, Y. Ouyang, J. F. Emery, and R. G. Giffard. 2009. Overexpression of mitochondrial Hsp70/Hsp75 in rat brain protects mitochondria, reduces oxidative stress, and protects from focal ischemia. *J Cereb Blood Flow Metab* 29:365-374.
11. Wadhwa, R., S. Takano, K. Kaur, C. C. Deocaris, O. M. Pereira-Smith, R. R. Reddel, and S. C. Kaul. 2006. Upregulation of mortalin/mthsp70/Grp75 contributes to human carcinogenesis. *Int J Cancer* 118:2973-2980.
12. Wadhwa, R., S. Takano, K. Taira, and S. C. Kaul. 2004. Reduction in mortalin level by its antisense expression causes senescence-like growth arrest in human immortalized cells. *J Gene Med* 6:439-444.
13. Ran, Q., R. Wadhwa, R. Kawai, S. C. Kaul, R. N. Sifers, R. J. Bick, J. R. Smith, and O. M. Pereira-Smith. 2000. Extramitochondrial localization of mortalin/mthsp70/PBP74/GRP75. *Biochem Biophys Res Commun* 275:174-179.
14. Takano, S., R. Wadhwa, Y. Yoshii, T. Nose, S. C. Kaul, and Y. Mitsui. 1997. Elevated levels of mortalin expression in human brain tumors. *Exp Cell Res* 237:38-45.
15. Dundas, S. R., L. C. Lawrie, P. H. Rooney, and G. I. Murray. 2005. Mortalin is over-expressed by colorectal adenocarcinomas and correlates with poor survival. *J Pathol* 205:74-81.
16. Pilzer, D., and Z. Fishelson. 2005. Mortalin/GRP75 promotes release of membrane vesicles from immune attacked cells and protection from complement-mediated lysis. *Int Immunol* 17:1239-1248.
17. Pilzer, D., M. Saar, K. Koya, and Z. Fishelson. 2010. Mortalin inhibitors sensitize K562 leukemia cells to complement-dependent cytotoxicity. *Int J Cancer* 126:1428-1435.
18. Pilzer, D., O. Gasser, O. Moskovich, J. A. Schifferli, and Z. Fishelson. 2005. Emission of membrane vesicles: roles in complement resistance, immunity and cancer. *Springer Semin Immunopathol* 27:375-387.
19. De Maio, A. 2011. Extracellular heat shock proteins, cellular export vesicles, and the Stress Observation System: a form of communication during injury, infection, and cell damage. It is never known how far a controversial finding will go! Dedicated to Ferruccio Ritossa. *Cell Stress Chaperones* 16:235-249.
20. Kocsis, J., B. Madaras, E. K. Toth, G. Fust, and Z. Prohaszka. 2010. Serum level of soluble 70-kD heat shock protein is associated with high mortality in patients with colorectal cancer without distant metastasis. *Cell Stress Chaperones* 15:143-151.
21. Kocsis, J., T. Meszaros, B. Madaras, E. K. Toth, S. Kamondi, P. Gal, L. Varga, Z. Prohaszka, and G. Fust.

2011. High levels of acute phase proteins and soluble 70 kDa heat shock proteins are independent and additive risk factors for mortality in colorectal cancer. *Cell Stress Chaperones* 16:49-55.
22. Yi, X., J. M. Luk, N. P. Lee, J. Peng, X. Leng, X. Y. Guan, G. K. Lau, L. Beretta, and S. T. Fan. 2008. Association of mortalin (HSPA9) with liver cancer metastasis and prediction for early tumor recurrence. *Mol Cell Proteomics* 7:315-325.
23. Chuma, M., M. Sakamoto, K. Yamazaki, T. Ohta, M. Ohki, M. Asaka, and S. Hirohashi. 2003. Expression profiling in multistage hepatocarcinogenesis: identification of HSP70 as a molecular marker of early hepatocellular carcinoma. *Hepatology* 37:198-207.
24. Sakamoto, M. 2009. Early HCC: diagnosis and molecular markers. *J Gastroenterol* 44 Suppl 19:108-111.
25. Behnsawy, H. M., H. Miyake, Y. Kusuda, and M. Fujisawa. 2011. Small interfering RNA targeting heat shock protein 70 enhances chemosensitivity in human bladder cancer cells. *Urol Oncol*.
26. Hightower, L. E., and P. T. Guidon, Jr. 1989. Selective release from cultured mammalian cells of heat-shock (stress) proteins that resemble glia-axon transfer proteins. *J Cell Physiol* 138:257-266.
27. Pockley, A. G., J. Shepherd, and J. M. Corton. 1998. Detection of heat shock protein 70 (Hsp70) and anti-Hsp70 antibodies in the serum of normal individuals. *Immunol Invest* 27:367-377.
28. Rozenberg P, Kocsis J, Saar M, Prohaszka Z, Hist G, Fishelson Z. Elevated levels of mitochondrial mortalin and cytosolic HSP70 in blood as risk factors in patients with colorectal cancer. *Int. J. Cancer.* 2013 Jul. 15; 133(2):514-8. doi: 10.1002/ijc.28029. Epub 2013 Feb. 12.

What is claimed is:

1. A method of measuring the level of soluble mortalin in a body fluid of a human subject diagnosed with a solid cancerous tumor, comprising:

(a) obtaining a body fluid sample from the human subject, said body fluid is selected from the group consisting of: blood, urine, tear, saliva, stool, cerebrospinal fluid, synovial fluid, lymph fluids, external secretions of a respiratory tract, external secretions of an intestinal tract external secretions of a genitourinary tract, milk and amniotic fluid, (b) contacting said body fluid sample with a monoclonal anti-mortalin antibody immobilized to a solid support, thereby producing an immobilized mortalin-monoclonal antibody complex, (c) contacting said immobilized mortalin-monoclonal antibody complex with a second, free anti-mortalin antibody which binds to a different epitope of said mortalin than said monoclonal anti-mortalin antibody, and specifically binds said immobilized mortalin-monoclonal antibody complex, thereby producing an immune complex comprising said second anti-mortalin antibody bound to said immobilized mortalin-monoclonal antibody complex;

(d) producing a linear dose-dependent calibration curve for detecting mortalin by sequentially:

(i) contacting a range of concentrations of purified recombinant mortalin with said immobilized monoclonal anti-mortalin antibody to produce immobilized purified mortalin-monoclonal antibody complex;

(ii) contacting said immobilized purified mortalin-monoclonal antibody complex with said second, free antibody to form an immune complex comprising said second antibody bound to said immobilized purified mortalin-monoclonal antibody complex, (iii) washing the immune complex of (ii), and (iv) detecting amounts of said purified recombinant mortalin in said immune complex of (ii), thereby producing a calibration curve, and (v) selecting a linear portion of the calibration curve of (iv), and (e) detecting the presence of said immune complex comprising said second anti-mortalin antibody of (c), within the linear range of the calibration curve of (d)(v), thereby measuring the level of the soluble mortalin in the body fluid of the human subject, and wherein said method gives a reproducible and sensitive detection of ≥0.25 ng of mortalin in human serum.

2. The method of claim 1, wherein said second, free antibody comprises a detectable moiety not found on said immobilized monoclonal anti-mortalin antibody, for detecting the presence of the immune complex comprising said second anti-mortalin antibody.

3. The method of claim 1, wherein said level of said second immune complex of claim 1(c) and 1(d)(ii) is measured by surface plasmon resonance.

4. The method of claim 1, wherein said level of said second immune complex of claim 1(c) and 1(d)(ii) is measured by capture Enzyme-linked immunosorbent assay (ELISA) or capture immunofluorescence.

5. The method of claim 1, wherein said presence of said immune complex of claim 1(c) comprising said second anti-mortalin antibody bound to said immobilized mortalin-monoclonal antibody complex or said immune complex of claim 1(d)(ii) comprising said second antibody bound to said immobilized purified mortalin-monoclonal antibody complex is detected by contacting with a secondary antibody specific for said second antibody and comprising a detectable moiety.

6. The method of claim 1, wherein said body fluid is a blood sample.

7. The method of claim 1, wherein said body fluid is a serum sample.

8. The method of claim 1, wherein said mortalin comprises the amino acid sequence set forth by SEQ ID NO:1.

9. The method of claim 1, wherein said detection of said second immune complex of claim 1(c) is followed by mass spectroscopy or nephelometry.

10. A method of measuring the level of soluble mortalin in a body fluid of a human subject, comprising:

(a) obtaining a body fluid sample from the human subject, said body fluid is selected from the group consisting of: blood, urine, tear, saliva, stool, cerebrospinal fluid, synovial fluid, lymph fluids, external secretions of a respiratory tract, external secretions of an intestinal tract external secretions of a genitourinary tract, milk and amniotic fluid, (b) contacting said body fluid sample with a monoclonal anti-mortalin antibody immobilized to a solid support, thereby producing an immobilized mortalin-monoclonal antibody complex, (c) contacting said immobilized mortalin-monoclonal antibody complex with a second, free anti-mortalin antibody which binds to a different epitope of said mortalin than said monoclonal anti-mortalin antibody, and specifically binds said immobilized mortalin-monoclonal antibody complex, thereby producing an immune complex comprising said second anti-mortalin antibody bound to said immobilized mortalin-monoclonal antibody complex;

(d) producing a linear dose-dependent calibration curve for detecting mortalin by sequentially:

(i) contacting a range of concentrations of purified recombinant mortalin with said immobilized monoclonal anti-mortalin antibody to produce immobilized purified mortalin-monoclonal antibody complex;

(ii) contacting said immobilized purified mortalin-monoclonal antibody complex with said second, free antibody to form an immune complex comprising said second antibody bound to said immobilized purified mortalin-monoclonal antibody complex, (iii) washing the immune complex of (ii), and (iv) detecting amounts of said purified recombinant mortalin in said immune complex of (ii), thereby producing a calibration curve, and (v) selecting a linear portion of the calibration curve of (iv) which gives a reproducible and sensitive detection of ≥0.25 ng of mortalin in human serum, and (e) detecting the presence of said immune complex comprising said second anti-mortalin antibody of (c), within the linear range of the calibration curve of (d)(v), thereby measuring the level of the soluble mortalin in the body fluid of the human subject.

11. The method of claim 10, wherein said subject is a subject diagnosed with a solid cancerous tumor.

* * * * *

SEQUENCE LISTING

<160> NUMBER OF SEQ ID NOS: 9

<210> SEQ ID NO 1
<211> LENGTH: 679
<212> TYPE: PRT
<213> ORGANISM: Homo sapiens

<400> SEQUENCE: 1

```
Met Ile Ser Ala Ser Arg Ala Ala Ala Arg Leu Val Gly Ala Ala
1               5                   10                  15

Ala Ser Arg Gly Pro Thr Ala Ala Arg His Gln Asp Ser Trp Asn Gly
                20                  25                  30

Leu Ser His Glu Ala Phe Arg Leu Val Ser Arg Arg Asp Tyr Ala Ser
            35                  40                  45

Glu Ala Ile Lys Gly Ala Val Val Gly Ile Asp Leu Gly Thr Thr Asn
        50                  55                  60

Ser Cys Val Ala Val Met Glu Gly Lys Gln Ala Lys Val Leu Glu Asn
65                  70                  75                  80

Ala Glu Gly Ala Arg Thr Thr Pro Ser Val Val Ala Phe Thr Ala Asp
                85                  90                  95

Gly Glu Arg Leu Val Gly Met Pro Ala Lys Arg Gln Ala Val Thr Asn
            100                 105                 110

Pro Asn Asn Thr Phe Tyr Ala Thr Lys Arg Leu Ile Gly Arg Arg Tyr
        115                 120                 125

Asp Asp Pro Glu Val Gln Lys Asp Ile Lys Asn Val Pro Phe Lys Ile
    130                 135                 140

Val Arg Ala Ser Asn Gly Asp Ala Trp Val Glu Ala His Gly Lys Leu
145                 150                 155                 160

Tyr Ser Pro Ser Gln Ile Gly Ala Phe Val Leu Met Lys Met Lys Glu
                165                 170                 175

Thr Ala Glu Asn Tyr Leu Gly His Thr Ala Lys Asn Ala Val Ile Thr
            180                 185                 190

Val Pro Ala Tyr Phe Asn Asp Ser Gln Arg Gln Ala Thr Lys Asp Ala
        195                 200                 205

Gly Gln Ile Ser Gly Leu Asn Val Leu Arg Val Ile Asn Glu Pro Thr
    210                 215                 220

Ala Ala Ala Leu Ala Tyr Gly Leu Asp Lys Ser Glu Asp Lys Val Ile
225                 230                 235                 240

Ala Val Tyr Asp Leu Gly Gly Gly Thr Phe Asp Ile Ser Ile Leu Glu
                245                 250                 255
```

-continued

```
Ile Gln Lys Gly Val Phe Glu Val Lys Ser Thr Asn Gly Asp Thr Phe
            260                 265                 270

Leu Gly Gly Glu Asp Phe Asp Gln Ala Leu Leu Arg His Ile Val Lys
            275                 280                 285

Glu Phe Lys Arg Glu Thr Gly Val Asp Leu Thr Lys Asp Asn Met Ala
            290                 295                 300

Leu Gln Arg Val Arg Glu Ala Glu Lys Ala Lys Cys Glu Leu Ser
305                 310                 315                 320

Ser Ser Val Gln Thr Asp Ile Asn Leu Pro Tyr Leu Thr Met Asp Ser
                325                 330                 335

Ser Gly Pro Lys His Leu Asn Met Lys Leu Thr Arg Ala Gln Phe Glu
            340                 345                 350

Gly Ile Val Thr Asp Leu Ile Arg Arg Thr Ile Ala Pro Cys Gln Lys
            355                 360                 365

Ala Met Gln Asp Ala Glu Val Ser Lys Ser Asp Ile Gly Glu Val Ile
            370                 375                 380

Leu Val Gly Gly Met Thr Arg Met Pro Lys Val Gln Gln Thr Val Gln
385                 390                 395                 400

Asp Leu Phe Gly Arg Ala Pro Ser Lys Ala Val Asn Pro Asp Glu Ala
                405                 410                 415

Val Ala Ile Gly Ala Ala Ile Gln Gly Gly Val Leu Ala Gly Asp Val
            420                 425                 430

Thr Asp Val Leu Leu Leu Asp Val Thr Pro Leu Ser Leu Gly Ile Glu
            435                 440                 445

Thr Leu Gly Gly Val Phe Thr Lys Leu Ile Asn Arg Asn Thr Thr Ile
            450                 455                 460

Pro Thr Lys Lys Ser Gln Val Phe Ser Thr Ala Ala Asp Gly Gln Thr
465                 470                 475                 480

Gln Val Glu Ile Lys Val Cys Gln Gly Glu Arg Glu Met Ala Gly Asp
                485                 490                 495

Asn Lys Leu Leu Gly Gln Phe Thr Leu Ile Gly Ile Pro Pro Ala Pro
            500                 505                 510

Arg Gly Val Pro Gln Ile Glu Val Thr Phe Asp Ile Asp Ala Asn Gly
            515                 520                 525

Ile Val His Val Ser Ala Lys Asp Lys Gly Thr Gly Arg Glu Gln Gln
            530                 535                 540

Ile Val Ile Gln Ser Ser Gly Gly Leu Ser Lys Asp Asp Ile Glu Asn
545                 550                 555                 560

Met Val Lys Asn Ala Glu Lys Tyr Ala Glu Glu Asp Arg Arg Lys Lys
                565                 570                 575

Glu Arg Val Glu Ala Val Asn Met Ala Glu Gly Ile Ile His Asp Thr
            580                 585                 590

Glu Thr Lys Met Glu Glu Phe Lys Asp Gln Leu Pro Ala Asp Glu Cys
            595                 600                 605

Asn Lys Leu Lys Glu Glu Ile Ser Lys Met Arg Glu Leu Leu Ala Arg
            610                 615                 620

Lys Asp Ser Glu Thr Gly Glu Asn Ile Arg Gln Ala Ala Ser Ser Leu
625                 630                 635                 640

Gln Gln Ala Ser Leu Lys Leu Phe Glu Met Ala Tyr Lys Lys Met Ala
                645                 650                 655
```

```
Ser Glu Arg Glu Gly Ser Gly Ser Ser Gly Thr Gly Glu Gln Lys Glu
        660                 665                 670

Asp Gln Lys Glu Glu Lys Gln
        675

<210> SEQ ID NO 2
<211> LENGTH: 3506
<212> TYPE: DNA
<213> ORGANISM: Homo sapiens

<400> SEQUENCE: 2
ttcctcccct ggactctttc tgagctcaga gccgccgcag ccgggacagg agggcaggct      60
ttctccaacc atcatgctgc ggagcatatt acctgtacgc cctggctccg ggagcggcag    120
tcgagtatcc tctggtcagg cggcgcgggc ggcgcctcag cggaagagcg ggcctctggg    180
ccgcagtgac caaccccgc ccctcacccc acgtggttgg aggtttccag aagcgctgcc     240
gccaccgcat cgcgcagctc tttgccgtcg gagcgcttgt ttgctgcctc gtactcctcc    300
atttatccgc catgataagt gccagccgag ctgcagcagc ccgtctcgtg ggcgccgcag    360
cctcccgggg ccctacggcc gcccgccacc aggatagctg aatggccctt agtcatgagg    420
cttttagact tgtttcaagg cgggattatg catcagaagc aatcaaggga gcagttgttg    480
gtattgattt gggtactacc aactcctgcg tggcagttat ggaaggtaaa caagcaaagg    540
tgctggagaa tgccgaaggt gccagaacca cccccttcagt tgtggccttt acagcagatg   600
gtgagcgact tgttggaatg ccggccaagc acaggctgt caccaaccca aacaatacat     660
tttatgctac caagcgtctc attggccggc gatatgatga tcctgaagta cagaaagaca    720
ttaaaaatgt tccctttaaa attgtccgtg cctccaatgg tgatgcctgg gttgaggctc    780
atgggaaatt gtattctccg agtcagattg agcatttgt gttgatgaag atgaaagaga     840
ctgcagaaaa ttacttgggg cacacagcaa aaaatgctgt gatcacagtc ccagcttatt    900
tcaatgactc gcagagacag gccactaaag atgctggcca gatatctgga ctgaatgtgc    960
ttcgggtgat taatgagccc acagctgctg ctcttgccta tggtctagac aaatcagaag   1020
acaaagtcat tgctgtatat gatttaggtg gtggaacttt tgatatttct atcctggaaa   1080
ttcagaaagg agtatttgag gtgaaatcca caaatgggga taccttctta ggtgggaag    1140 actttgacca ggccttgcta cggcacattg tgaaggagtt caagagagag caggggttg    1200 atttgactaa agacaacatg gcacttcaga gggtacggga agctgctgaa aaggctaaat   1260
gtgaactctc ctcatctgtg cagactgaca tcaatttgcc ctatcttaca atggattctt   1320
ctggacccaa gcatttgaat atgaagttga cccgtgctca atttgaaggg attgtcactg   1380
atctaatcag aaggactatc gctccatgcc aaaaagctat gcaagatgca gaagtcagca   1440
agagtgacat aggagaagtg attcttgtgg gtggcatgac taggatgccc aaggttcagc   1500
agactgtaca ggatctttt ggcagagccc aagtaaagc tgtcaatcct gatgaggctg     1560
tggccattgg agctgccatt caggaggtg tgttggccgg cgatgtcacg gatgtgctgc    1620
tccttgatgt cactcccctg tctctgggta ttgaaactct aggaggtgtc tttaccaaac   1680
ttattaatag gaataccact attccaacca gaaagagcca ggtattctct actgccgctg   1740
atggtcaaac gcaagtggaa attaaagtgt gtcagggtga agagagatg gctggagaca    1800 acaaactcct ggacagttt actttgattg gaattccacc agccctcgt ggagttcctc     1860 agattgaagt tacatttgac attgatgcca atggatagt acatgttct gctaaagata     1920 aaggcacagg acgtgagcag cagattgtaa tccagtcttc tggtggatta agcaaagatg   1980
```

-continued

| | |
|---|---|
| atattgaaaa tatggttaaa aatgcagaga aatatgctga agaagaccgg cgaaagaagg | 2040 |
| aacgagttga agcagttaat atggctgaag gaatcattca cgacacagaa accaagatgg | 2100 |
| aagaattcaa ggaccaatta cctgctgatg agtgcaacaa gctgaaagaa gagatttcca | 2160 |
| aaatgaggga gctcctggct agaaaagaca gcgaaacagg agaaaatatt agacaggcag | 2220 |
| catcctctct tcagcaggca tcactgaagc tgttcgaaat ggcatacaaa aagatggcat | 2280 |
| ctgagcgaga aggctctgga agttctggca ctggggaaca aaaggaagat caaaaggagg | 2340 |
| aaaaacagta ataatagcag aaattttgaa gccagaagga caacatatga agcttaggag | 2400 |
| tgaagagact tcctgagcag aaatgggcga acttcagtct ttttactgtg tttttgcagt | 2460 |
| attctatata taatttcctt aatttgtaaa tttagtgacc attagctagt gatcatttaa | 2520 |
| tggacagtga ttctaacagt ataaagttca caatattcta tgtccctagc ctgtcatttt | 2580 |
| tcagctgcat gtaaaaggag gtaggatgaa ttgatcatta taaagattta actattttat | 2640 |
| gctgaagtga ccatatttc aagggggtgaa accatctcgc acacagcaat gaaggtagtc | 2700 |
| atccatagac ttgaaatgag accacatatg gggatgagat ccttctagtt agcctagtac | 2760 |
| tgctgtactg gcctgtatgt acatgggggtc cttcaactga ggccttgcaa gtcaagctgg | 2820 |
| ctgtgccatg tttgtagatg gggcagagga atctagaaca atgggaaact tagctattta | 2880 |
| tattaggtac agctattaaa acaaggtagg aatgaggcta gacctttaac ttccctaagg | 2940 |
| catactttc tagctacctt ctgccctgtg tctggcacct acatccttga tgattgttct | 3000 |
| cttacccatt ctggaatttt tttttttta aataaataca gaaagcatct tgatctcttg | 3060 |
| tttgtgaggg gtgatgccct gagatttagc ttcaagaata tgccatggct catgcttccc | 3120 |
| atatttccca aagagggaaa tacaggattt gctaacactg gttaaaaatg caaattcaag | 3180 |
| atttggaagg gctgttataa tgaaataatg agcagtatca gcatgtgcaa atcttgtttg | 3240 |
| aaggatttta ttttctcccc ttagaccttt ggtacattta gaatcttgaa agtttctaga | 3300 |
| tctctaacat gaaagtttct agatctctaa catgaaagtt tttagatctc taacatgaaa | 3360 |
| accaaggtgg ctattttcag gttgctttca gctccaagta gaaataacca gaattggctt | 3420 |
| acattaaaga aactgcatct agaaataagt cctaagatac tatttctatg gctcaaaaat | 3480 |
| aaaaggaacc cagatttctt tccta | 3506 |

<210> SEQ ID NO 3
<211> LENGTH: 641
<212> TYPE: PRT
<213> ORGANISM: Homo sapiens

<400> SEQUENCE: 3

Met Ala Lys Ala Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

```
Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510
```

```
Glu Glu Ile Glu Arg Met Val Gln Glu Ala Lys Tyr Lys Ala Glu
        515                 520                 525

Asp Glu Val Gln Arg Glu Arg Val Ser Ala Lys Asn Ala Leu Glu Ser
530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
        595                 600                 605

Gly Leu Tyr Gln Gly Ala Gly Gly Pro Gly Pro Gly Gly Phe Gly Ala
    610                 615                 620

Gln Gly Pro Lys Gly Gly Ser Gly Ser Gly Pro Thr Ile Glu Glu Val
625                 630                 635                 640

Asp

<210> SEQ ID NO 4
<211> LENGTH: 641
<212> TYPE: PRT
<213> ORGANISM: Homo sapiens

<400> SEQUENCE: 4

Met Ala Lys Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Leu Asn Pro Gln
        50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240
```

```
                Phe Val Glu Glu Phe Lys Arg Lys His Lys Lys Asp Ile Ser Gln Asn
                                245                 250                 255

Lys Arg Ala Val Arg Arg Leu Arg Thr Ala Cys Glu Arg Ala Lys Arg
                            260                 265                 270

Thr Leu Ser Ser Ser Thr Gln Ala Ser Leu Glu Ile Asp Ser Leu Phe
                            275                 280                 285

Glu Gly Ile Asp Phe Tyr Thr Ser Ile Thr Arg Ala Arg Phe Glu Glu
                            290                 295                 300

Leu Cys Ser Asp Leu Phe Arg Ser Thr Leu Glu Pro Val Glu Lys Ala
                305                 310                 315                 320

Leu Arg Asp Ala Lys Leu Asp Lys Ala Gln Ile His Asp Leu Val Leu
                                325                 330                 335

Val Gly Gly Ser Thr Arg Ile Pro Lys Val Gln Lys Leu Leu Gln Asp
                                340                 345                 350

Phe Phe Asn Gly Arg Asp Leu Asn Lys Ser Ile Asn Pro Asp Glu Ala
                                355                 360                 365

Val Ala Tyr Gly Ala Ala Val Gln Ala Ala Ile Leu Met Gly Asp Lys
                            370                 375                 380

Ser Glu Asn Val Gln Asp Leu Leu Leu Leu Asp Val Ala Pro Leu Ser
                385                 390                 395                 400

Leu Gly Leu Glu Thr Ala Gly Gly Val Met Thr Ala Leu Ile Lys Arg
                                405                 410                 415

Asn Ser Thr Ile Pro Thr Lys Gln Thr Gln Ile Phe Thr Thr Tyr Ser
                                420                 425                 430

Asp Asn Gln Pro Gly Val Leu Ile Gln Val Tyr Glu Gly Glu Arg Ala
                                435                 440                 445

Met Thr Lys Asp Asn Asn Leu Leu Gly Arg Phe Glu Leu Ser Gly Ile
                            450                 455                 460

Pro Pro Ala Pro Arg Gly Val Pro Gln Ile Glu Val Thr Phe Asp Ile
                465                 470                 475                 480

Asp Ala Asn Gly Ile Leu Asn Val Thr Ala Thr Asp Lys Ser Thr Gly
                                485                 490                 495

Lys Ala Asn Lys Ile Thr Ile Thr Asn Asp Lys Gly Arg Leu Ser Lys
                                500                 505                 510

Glu Glu Ile Glu Arg Met Val Gln Glu Ala Glu Lys Tyr Lys Ala Glu
                                515                 520                 525

Asp Glu Val Gln Arg Glu Arg Val Ser Ala Lys Asn Ala Leu Glu Ser
                            530                 535                 540

Tyr Ala Phe Asn Met Lys Ser Ala Val Glu Asp Glu Gly Leu Lys Gly
                545                 550                 555                 560

Lys Ile Ser Glu Ala Asp Lys Lys Lys Val Leu Asp Lys Cys Gln Glu
                                565                 570                 575

Val Ile Ser Trp Leu Asp Ala Asn Thr Leu Ala Glu Lys Asp Glu Phe
                            580                 585                 590

Glu His Lys Arg Lys Glu Leu Glu Gln Val Cys Asn Pro Ile Ile Ser
                            595                 600                 605

Gly Leu Tyr Gln Gly Ala Gly Gly Pro Gly Pro Gly Gly Phe Gly Ala
                            610                 615                 620

Gln Gly Pro Lys Gly Gly Ser Gly Ser Gly Pro Thr Ile Glu Glu Val
                625                 630                 635                 640

Asp
```

```
<210> SEQ ID NO 5
<211> LENGTH: 639
<212> TYPE: PRT
<213> ORGANISM: Homo sapiens

<400> SEQUENCE: 5
```

| | | | | | | | | | | | | | | | |
|---|---|---|---|---|---|---|---|---|---|---|---|---|---|---|---|
| Met | Ser | Ala | Arg | Gly | Pro | Ala | Ile | Gly | Ile | Asp | Leu | Gly | Thr | Thr | Tyr |
| 1 | | | | 5 | | | | | 10 | | | | | 15 | |
| Ser | Cys | Val | Gly | Val | Phe | Gln | His | Gly | Lys | Val | Glu | Ile | Ile | Ala | Asn |
| | | | 20 | | | | | 25 | | | | | 30 | | |
| Asp | Gln | Gly | Asn | Arg | Thr | Thr | Pro | Ser | Tyr | Val | Ala | Phe | Thr | Asp | Thr |
| | | | 35 | | | | 40 | | | | | 45 | | | |
| Glu | Arg | Leu | Ile | Gly | Asp | Ala | Ala | Lys | Asn | Gln | Val | Ala | Met | Asn | Pro |
| | 50 | | | | | 55 | | | | | 60 | | | | |
| Thr | Asn | Thr | Ile | Phe | Asp | Ala | Lys | Arg | Leu | Ile | Gly | Arg | Lys | Phe | Glu |
| 65 | | | | | 70 | | | | | 75 | | | | | 80 |
| Asp | Ala | Thr | Val | Gln | Ser | Asp | Met | Lys | His | Trp | Pro | Phe | Arg | Val | Val |
| | | | | 85 | | | | | 90 | | | | | 95 | |
| Ser | Glu | Gly | Gly | Lys | Pro | Lys | Val | Gln | Val | Glu | Tyr | Lys | Gly | Glu | Thr |
| | | | 100 | | | | | 105 | | | | | 110 | | |
| Lys | Thr | Phe | Phe | Pro | Glu | Glu | Ile | Ser | Ser | Met | Val | Leu | Thr | Lys | Met |
| | | | 115 | | | | | 120 | | | | | 125 | | |
| Lys | Glu | Ile | Ala | Glu | Ala | Tyr | Leu | Gly | Lys | Val | His | Ser | Ala | Val |
| | 130 | | | | | 135 | | | | | 140 | | | | |
| Ile | Thr | Val | Pro | Ala | Tyr | Phe | Asn | Asp | Ser | Gln | Arg | Gln | Ala | Thr | Lys |
| 145 | | | | | 150 | | | | | 155 | | | | | 160 |
| Asp | Ala | Gly | Thr | Ile | Thr | Gly | Leu | Asn | Val | Leu | Arg | Ile | Ile | Asn | Glu |
| | | | | 165 | | | | | 170 | | | | | 175 | |
| Pro | Thr | Ala | Ala | Ala | Ile | Ala | Tyr | Gly | Leu | Asp | Lys | Lys | Gly | Cys | Ala |
| | | | 180 | | | | | 185 | | | | | 190 | | |
| Gly | Gly | Glu | Lys | Asn | Val | Leu | Ile | Phe | Asp | Leu | Gly | Gly | Gly | Thr | Phe |
| | | | 195 | | | | | 200 | | | | | 205 | | |
| Asp | Val | Ser | Ile | Leu | Thr | Ile | Glu | Asp | Gly | Ile | Phe | Glu | Val | Lys | Ser |
| | 210 | | | | | 215 | | | | | 220 | | | | |
| Thr | Ala | Gly | Asp | Thr | His | Leu | Gly | Gly | Glu | Asp | Phe | Asp | Asn | Arg | Met |
| 225 | | | | | 230 | | | | | 235 | | | | | 240 |
| Val | Ser | His | Leu | Ala | Glu | Glu | Phe | Lys | Arg | Lys | His | Lys | Lys | Asp | Ile |
| | | | | 245 | | | | | 250 | | | | | 255 | |
| Gly | Pro | Asn | Lys | Arg | Ala | Val | Arg | Arg | Leu | Arg | Thr | Ala | Cys | Glu | Arg |
| | | | 260 | | | | | 265 | | | | | 270 | | |
| Ala | Lys | Arg | Thr | Leu | Ser | Ser | Ser | Thr | Gln | Ala | Ser | Ile | Glu | Ile | Asp |
| | | | 275 | | | | | 280 | | | | | 285 | | |
| Ser | Leu | Tyr | Glu | Gly | Val | Asp | Phe | Tyr | Thr | Ser | Ile | Thr | Arg | Ala | Arg |
| | 290 | | | | | 295 | | | | | 300 | | | | |
| Phe | Glu | Glu | Leu | Asn | Ala | Asp | Leu | Phe | Arg | Gly | Thr | Leu | Glu | Pro | Val |
| 305 | | | | | 310 | | | | | 315 | | | | | 320 |
| Glu | Lys | Ala | Leu | Arg | Asp | Ala | Lys | Leu | Asp | Lys | Gly | Gln | Ile | Gln | Glu |
| | | | | 325 | | | | | 330 | | | | | 335 | |
| Ile | Val | Leu | Val | Gly | Gly | Ser | Thr | Arg | Ile | Pro | Lys | Ile | Gln | Lys | Leu |
| | | | 340 | | | | | 345 | | | | | 350 | | |
| Leu | Gln | Asp | Phe | Phe | Asn | Gly | Lys | Glu | Leu | Asn | Lys | Ser | Ile | Asn | Pro |
| | | | 355 | | | | | 360 | | | | | 365 | | |
| Asp | Glu | Ala | Val | Ala | Tyr | Gly | Ala | Ala | Val | Gln | Ala | Ala | Ile | Leu | Ile |
| | 370 | | | | | 375 | | | | | 380 | | | | |

Gly Asp Lys Ser Glu Asn Val Gln Asp Leu Leu Leu Asp Val Thr
385                 390                 395                 400

Pro Leu Ser Leu Gly Ile Glu Thr Ala Gly Val Met Thr Pro Leu
            405                 410                 415

Ile Lys Arg Asn Thr Thr Ile Pro Thr Lys Gln Thr Gln Thr Phe Thr
        420                 425                 430

Thr Tyr Ser Asp Asn Gln Ser Ser Val Leu Val Gln Val Tyr Glu Gly
            435                 440                 445

Glu Arg Ala Met Thr Lys Asp Asn Asn Leu Leu Gly Lys Phe Asp Leu
    450                 455                 460

Thr Gly Ile Pro Pro Ala Pro Arg Gly Val Pro Gln Ile Glu Val Thr
465                 470                 475                 480

Phe Asp Ile Asp Ala Asn Gly Ile Leu Asn Val Thr Ala Ala Asp Lys
                485                 490                 495

Ser Thr Gly Lys Glu Asn Lys Ile Thr Ile Thr Asn Asp Lys Gly Arg
            500                 505                 510

Leu Ser Lys Asp Asp Ile Asp Arg Met Val Gln Glu Ala Glu Arg Tyr
        515                 520                 525

Lys Ser Glu Asp Glu Ala Asn Arg Asp Arg Val Ala Ala Lys Asn Ala
530                 535                 540

Leu Glu Ser Tyr Thr Tyr Asn Ile Lys Gln Thr Val Glu Asp Glu Lys
545                 550                 555                 560

Leu Arg Gly Lys Ile Ser Glu Gln Asp Lys Asn Lys Ile Leu Asp Lys
                565                 570                 575

Cys Gln Glu Val Ile Asn Trp Leu Asp Arg Asn Gln Met Ala Glu Lys
            580                 585                 590

Asp Glu Tyr Glu His Lys Gln Lys Glu Leu Glu Arg Val Cys Asn Pro
        595                 600                 605

Ile Ile Ser Lys Leu Tyr Gln Gly Gly Pro Gly Gly Gly Ser Gly Gly
610                 615                 620

Gly Gly Ser Gly Ala Ser Gly Gly Pro Thr Ile Glu Glu Val Asp
625                 630                 635

<210> SEQ ID NO 6
<211> LENGTH: 641
<212> TYPE: PRT
<213> ORGANISM: Homo sapiens

<400> SEQUENCE: 6

Met Ala Thr Ala Lys Gly Ile Ala Ile Gly Ile Asp Leu Gly Thr Thr
1               5                   10                  15

Tyr Ser Cys Val Gly Val Phe Gln His Gly Lys Val Glu Ile Ile Ala
            20                  25                  30

Asn Asp Gln Gly Asn Arg Thr Thr Pro Ser Tyr Val Ala Phe Thr Asp
        35                  40                  45

Thr Glu Arg Leu Ile Gly Asp Ala Ala Lys Asn Gln Val Ala Met Asn
    50                  55                  60

Pro Gln Asn Thr Val Phe Asp Ala Lys Arg Leu Ile Gly Arg Lys Phe
65                  70                  75                  80

Asn Asp Pro Val Val Gln Ala Asp Met Lys Leu Trp Pro Phe Gln Val
                85                  90                  95

Ile Asn Glu Gly Gly Lys Pro Lys Val Leu Val Ser Tyr Lys Gly Glu
            100                 105                 110

Asn Lys Ala Phe Tyr Pro Glu Glu Ile Ser Ser Met Val Leu Thr Lys
        115                 120                 125

```
Leu Lys Glu Thr Ala Glu Ala Phe Leu Gly His Pro Val Thr Asn Ala
    130                 135                 140

Val Ile Thr Val Pro Ala Tyr Phe Asn Asp Ser Gln Arg Gln Ala Thr
145                 150                 155                 160

Lys Asp Ala Gly Val Ile Ala Gly Leu Asn Val Leu Arg Ile Ile Asn
                165                 170                 175

Glu Pro Thr Ala Ala Ala Ile Ala Tyr Gly Leu Asp Lys Gly Gly Gln
            180                 185                 190

Gly Glu Arg His Val Leu Ile Phe Asp Leu Gly Gly Thr Phe Asp
            195                 200                 205

Val Ser Ile Leu Thr Ile Asp Asp Gly Ile Phe Glu Val Lys Ala Thr
210                 215                 220

Ala Gly Asp Thr His Leu Gly Gly Glu Asp Phe Asp Asn Arg Leu Val
225                 230                 235                 240

Ser His Phe Val Glu Glu Phe Lys Arg Lys His Lys Lys Asp Ile Ser
                245                 250                 255

Gln Asn Lys Arg Ala Val Arg Arg Leu Arg Thr Ala Cys Glu Arg Ala
            260                 265                 270

Lys Arg Thr Leu Ser Ser Ser Thr Gln Ala Asn Leu Glu Ile Asp Ser
        275                 280                 285

Leu Tyr Glu Gly Ile Asp Phe Tyr Thr Ser Ile Thr Arg Ala Arg Phe
    290                 295                 300

Glu Glu Leu Cys Ala Asp Leu Phe Arg Gly Thr Leu Glu Pro Val Glu
305                 310                 315                 320

Lys Ala Leu Arg Asp Ala Lys Met Asp Lys Ala Lys Ile His Asp Ile
                325                 330                 335

Val Leu Val Gly Gly Ser Thr Arg Ile Pro Lys Val Gln Arg Leu Leu
            340                 345                 350

Gln Asp Tyr Phe Asn Gly Arg Asp Leu Asn Lys Ser Ile Asn Pro Asp
        355                 360                 365

Glu Ala Val Ala Tyr Gly Ala Ala Val Gln Ala Ala Ile Leu Met Gly
    370                 375                 380

Asp Lys Ser Glu Lys Val Gln Asp Leu Leu Leu Leu Asp Val Ala Pro
385                 390                 395                 400

Leu Ser Leu Gly Leu Glu Thr Ala Gly Gly Val Met Thr Ala Leu Ile
                405                 410                 415

Lys Arg Asn Ser Thr Ile Pro Thr Lys Gln Thr Gln Ile Phe Thr Thr
            420                 425                 430

Tyr Ser Asp Asn Gln Pro Gly Val Leu Ile Gln Val Tyr Glu Gly Glu
        435                 440                 445

Arg Ala Met Thr Lys Asp Asn Asn Leu Leu Gly Arg Phe Asp Leu Thr
    450                 455                 460

Gly Ile Pro Pro Ala Pro Arg Gly Val Pro Gln Ile Glu Val Thr Phe
465                 470                 475                 480

Asp Ile Asp Ala Asn Gly Ile Leu Asn Val Thr Ala Thr Asp Lys Ser
                485                 490                 495

Thr Gly Lys Val Asn Lys Ile Thr Ile Thr Asn Asp Lys Gly Arg Leu
            500                 505                 510

Ser Lys Glu Glu Ile Glu Arg Met Val Leu Asp Ala Glu Lys Tyr Lys
        515                 520                 525

Ala Glu Asp Glu Val Gln Arg Glu Lys Ile Ala Ala Lys Asn Ala Leu
    530                 535                 540
```

-continued

```
Glu Ser Tyr Ala Phe Asn Met Lys Ser Val Val Ser Asp Glu Gly Leu
545                 550                 555                 560

Lys Gly Lys Ile Ser Glu Ser Asp Lys Asn Lys Ile Leu Asp Lys Cys
            565                 570                 575

Asn Glu Leu Leu Ser Trp Leu Glu Val Asn Gln Leu Ala Glu Lys Asp
        580                 585                 590

Glu Phe Asp His Lys Arg Lys Glu Leu Glu Gln Met Cys Asn Pro Ile
    595                 600                 605

Ile Thr Lys Leu Tyr Gln Gly Gly Cys Thr Gly Pro Ala Cys Gly Thr
610                 615                 620

Gly Tyr Val Pro Gly Arg Pro Ala Thr Gly Pro Thr Ile Glu Glu Val
625                 630                 635                 640

Asp

<210> SEQ ID NO 7
<211> LENGTH: 643
<212> TYPE: PRT
<213> ORGANISM: Homo sapiens

<400> SEQUENCE: 7

Met Gln Ala Pro Arg Glu Leu Ala Val Gly Ile Asp Leu Gly Thr Thr
1               5                   10                  15

Tyr Ser Cys Val Gly Val Phe Gln Gln Gly Arg Val Glu Ile Leu Ala
            20                  25                  30

Asn Asp Gln Gly Asn Arg Thr Thr Pro Ser Tyr Val Ala Phe Thr Asp
        35                  40                  45

Thr Glu Arg Leu Val Gly Asp Ala Ala Lys Ser Gln Ala Ala Leu Asn
    50                  55                  60

Pro His Asn Thr Val Phe Asp Ala Lys Arg Leu Ile Gly Arg Lys Phe
65                  70                  75                  80

Ala Asp Thr Thr Val Gln Ser Asp Met Lys His Trp Pro Phe Arg Val
                85                  90                  95

Val Ser Glu Gly Gly Lys Pro Lys Val Arg Val Cys Tyr Arg Gly Glu
            100                 105                 110

Asp Lys Thr Phe Tyr Pro Glu Glu Ile Ser Ser Met Val Leu Ser Lys
        115                 120                 125

Met Lys Glu Thr Ala Glu Ala Tyr Leu Gly Gln Pro Val Lys His Ala
    130                 135                 140

Val Ile Thr Val Pro Ala Tyr Phe Asn Asp Ser Gln Arg Gln Ala Thr
145                 150                 155                 160

Lys Asp Ala Gly Ala Ile Ala Gly Leu Asn Val Leu Arg Ile Ile Asn
                165                 170                 175

Glu Pro Thr Ala Ala Ala Ile Ala Tyr Gly Leu Asp Arg Arg Gly Ala
            180                 185                 190

Gly Glu Arg Asn Val Leu Ile Phe Asp Leu Gly Gly Gly Thr Phe Asp
        195                 200                 205

Val Ser Val Leu Ser Ile Asp Ala Gly Val Phe Glu Val Lys Ala Thr
    210                 215                 220

Ala Gly Asp Thr His Leu Gly Gly Glu Asp Phe Asp Asn Arg Leu Val
225                 230                 235                 240

Asn His Phe Met Glu Glu Phe Arg Arg Lys His Gly Lys Asp Leu Ser
                245                 250                 255

Gly Asn Lys Arg Ala Leu Arg Arg Leu Arg Thr Ala Cys Glu Arg Ala
            260                 265                 270
```

```
Lys Arg Thr Leu Ser Ser Ser Thr Gln Ala Thr Leu Glu Ile Asp Ser
            275                 280                 285

Leu Phe Glu Gly Val Asp Phe Tyr Thr Ser Ile Thr Arg Ala Arg Phe
290                 295                 300

Glu Glu Leu Cys Ser Asp Leu Phe Arg Ser Thr Leu Glu Pro Val Glu
305                 310                 315                 320

Lys Ala Leu Arg Asp Ala Lys Leu Asp Lys Ala Gln Ile His Asp Val
                325                 330                 335

Val Leu Val Gly Gly Ser Thr Arg Ile Pro Lys Val Gln Lys Leu Leu
            340                 345                 350

Gln Asp Phe Phe Asn Gly Lys Glu Leu Asn Lys Ser Ile Asn Pro Asp
        355                 360                 365

Glu Ala Val Ala Tyr Gly Ala Ala Val Gln Ala Ala Val Leu Met Gly
    370                 375                 380

Asp Lys Cys Glu Lys Val Gln Asp Leu Leu Leu Leu Asp Val Ala Pro
385                 390                 395                 400

Leu Ser Leu Gly Leu Glu Thr Ala Gly Gly Val Met Thr Thr Leu Ile
                405                 410                 415

Gln Arg Asn Ala Thr Ile Pro Thr Lys Gln Thr Gln Thr Phe Thr Thr
            420                 425                 430

Tyr Ser Asp Asn Gln Pro Gly Val Phe Ile Gln Val Tyr Glu Gly Glu
        435                 440                 445

Arg Ala Met Thr Lys Asp Asn Asn Leu Leu Gly Arg Phe Glu Leu Ser
    450                 455                 460

Gly Ile Pro Pro Ala Pro Arg Gly Val Pro Gln Ile Glu Val Thr Phe
465                 470                 475                 480

Asp Ile Asp Ala Asn Gly Ile Leu Ser Val Thr Ala Thr Asp Arg Ser
                485                 490                 495

Thr Gly Lys Ala Asn Lys Ile Thr Ile Thr Asn Asp Lys Gly Arg Leu
            500                 505                 510

Ser Lys Glu Glu Val Glu Arg Met Val His Glu Ala Glu Gln Tyr Lys
        515                 520                 525

Ala Glu Asp Glu Ala Gln Arg Asp Arg Val Ala Ala Lys Asn Ser Leu
    530                 535                 540

Glu Ala His Val Phe His Val Lys Gly Ser Leu Gln Glu Glu Ser Leu
545                 550                 555                 560

Arg Asp Lys Ile Pro Glu Asp Arg Arg Lys Met Gln Asp Lys Cys
                565                 570                 575

Arg Glu Val Leu Ala Trp Leu Glu His Asn Gln Leu Ala Glu Lys Glu
        580                 585                 590

Glu Tyr Glu His Gln Lys Arg Glu Leu Glu Gln Ile Cys Arg Pro Ile
    595                 600                 605

Phe Ser Arg Leu Tyr Gly Gly Pro Gly Val Pro Gly Gly Ser Ser Cys
610                 615                 620

Gly Thr Gln Ala Arg Gln Gly Asp Pro Ser Thr Gly Pro Ile Ile Glu
625                 630                 635                 640

Glu Val Asp

<210> SEQ ID NO 8
<211> LENGTH: 646
<212> TYPE: PRT
<213> ORGANISM: Homo sapiens
```

```
<400> SEQUENCE: 8

Met Ser Lys Gly Pro Ala Val Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Met Asn Pro Thr
    50                  55                  60

Asn Thr Val Phe Asp Ala Lys Arg Leu Ile Gly Arg Arg Phe Asp Asp
65                  70                  75                  80

Ala Val Val Gln Ser Asp Met Lys His Trp Pro Phe Met Val Val Asn
                85                  90                  95

Asp Ala Gly Arg Pro Lys Val Gln Val Glu Tyr Lys Gly Glu Thr Lys
            100                 105                 110

Ser Phe Tyr Pro Glu Glu Val Ser Ser Met Val Leu Thr Lys Met Lys
        115                 120                 125

Glu Ile Ala Glu Ala Tyr Leu Gly Lys Thr Val Thr Asn Ala Val Val
    130                 135                 140

Thr Val Pro Ala Tyr Phe Asn Asp Ser Gln Arg Gln Ala Thr Lys Asp
145                 150                 155                 160

Ala Gly Thr Ile Ala Gly Leu Asn Val Leu Arg Ile Ile Asn Glu Pro
                165                 170                 175

Thr Ala Ala Ala Ile Ala Tyr Gly Leu Asp Lys Lys Val Gly Ala Glu
            180                 185                 190

Arg Asn Val Leu Ile Phe Asp Leu Gly Gly Gly Thr Phe Asp Val Ser
        195                 200                 205

Ile Leu Thr Ile Glu Asp Gly Ile Phe Glu Val Lys Ser Thr Ala Gly
    210                 215                 220

Asp Thr His Leu Gly Gly Glu Asp Phe Asp Asn Arg Met Val Asn His
225                 230                 235                 240

Phe Ile Ala Glu Phe Lys Arg Lys His Lys Lys Asp Ile Ser Glu Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Ile Glu Ile Asp Ser Leu Tyr
        275                 280                 285

Glu Gly Ile Asp Phe Tyr Thr Ser Ile Thr Arg Ala Arg Phe Glu Glu
    290                 295                 300

Leu Asn Ala Asp Leu Phe Arg Gly Thr Leu Asp Pro Val Glu Lys Ala
305                 310                 315                 320

Leu Arg Asp Ala Lys Leu Asp Lys Ser Gln Ile His Asp Ile Val Leu
                325                 330                 335

Val Gly Gly Ser Thr Arg Ile Pro Lys Ile Gln Lys Leu Leu Gln Asp
            340                 345                 350

Phe Phe Asn Gly Lys Glu Leu Asn Lys Ser Ile Asn Pro Asp Glu Ala
        355                 360                 365

Val Ala Tyr Gly Ala Ala Val Gln Ala Ala Ile Leu Ser Gly Asp Lys
    370                 375                 380

Ser Glu Asn Val Gln Asp Leu Leu Leu Leu Asp Val Thr Pro Leu Ser
385                 390                 395                 400

Leu Gly Ile Glu Thr Ala Gly Gly Val Met Thr Val Leu Ile Lys Arg
                405                 410                 415
```

```
Asn Thr Thr Ile Pro Thr Lys Gln Thr Gln Thr Phe Thr Thr Tyr Ser
            420             425             430

Asp Asn Gln Pro Gly Val Leu Ile Gln Val Tyr Glu Gly Glu Arg Ala
        435             440             445

Met Thr Lys Asp Asn Asn Leu Leu Gly Lys Phe Glu Leu Thr Gly Ile
    450             455             460

Pro Pro Ala Pro Arg Gly Val Pro Gln Ile Glu Val Thr Phe Asp Ile
465             470             475             480

Asp Ala Asn Gly Ile Leu Asn Val Ser Ala Val Asp Lys Ser Thr Gly
            485             490             495

Lys Glu Asn Lys Ile Thr Ile Thr Asn Asp Lys Gly Arg Leu Ser Lys
        500             505             510

Glu Asp Ile Glu Arg Met Val Gln Glu Ala Glu Lys Tyr Lys Ala Glu
    515             520             525

Asp Glu Lys Gln Arg Asp Lys Val Ser Ser Lys Asn Ser Leu Glu Ser
530             535             540

Tyr Ala Phe Asn Met Lys Ala Thr Val Glu Asp Glu Lys Leu Gln Gly
545             550             555             560

Lys Ile Asn Asp Glu Asp Lys Gln Lys Ile Leu Asp Lys Cys Asn Glu
            565             570             575

Ile Ile Asn Trp Leu Asp Lys Asn Gln Thr Ala Glu Lys Glu Glu Phe
        580             585             590

Glu His Gln Gln Lys Glu Leu Glu Lys Val Cys Asn Pro Ile Ile Thr
    595             600             605

Lys Leu Tyr Gln Ser Ala Gly Gly Met Pro Gly Gly Met Pro Gly Gly
610             615             620

Phe Pro Gly Gly Gly Ala Pro Pro Ser Gly Gly Ala Ser Ser Gly Pro
625             630             635             640

Thr Ile Glu Glu Val Asp
            645

<210> SEQ ID NO 9
<211> LENGTH: 493
<212> TYPE: PRT
<213> ORGANISM: Homo sapiens

<400> SEQUENCE: 9

Met Ser Lys Gly Pro Ala Val Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Met Asn Pro Thr
    50                  55                  60

Asn Thr Val Phe Asp Ala Lys Arg Leu Ile Gly Arg Arg Phe Asp Asp
65                  70                  75                  80

Ala Val Val Gln Ser Asp Met Lys His Trp Pro Phe Met Val Val Asn
                85                  90                  95

Asp Ala Gly Arg Pro Lys Val Gln Val Glu Tyr Lys Gly Glu Thr Lys
            100                 105                 110

Ser Phe Tyr Pro Glu Glu Val Ser Ser Met Val Leu Thr Lys Met Lys
        115                 120                 125

Glu Ile Ala Glu Ala Tyr Leu Gly Lys Thr Val Thr Asn Ala Val Val
    130                 135                 140
```

-continued

```
Thr Val Pro Ala Tyr Phe Asn Asp Ser Gln Arg Gln Ala Thr Lys Asp
145                 150                 155                 160

Ala Gly Thr Ile Ala Gly Leu Asn Val Leu Arg Ile Ile Asn Glu Pro
                165                 170                 175

Thr Ala Ala Ala Ile Ala Tyr Gly Leu Asp Lys Lys Val Gly Ala Glu
            180                 185                 190

Arg Asn Val Leu Ile Phe Asp Leu Gly Gly Gly Thr Phe Asp Val Ser
        195                 200                 205

Ile Leu Thr Ile Glu Asp Gly Ile Phe Glu Val Lys Ser Thr Ala Gly
    210                 215                 220

Asp Thr His Leu Gly Gly Glu Asp Phe Asp Asn Arg Met Val Asn His
225                 230                 235                 240

Phe Ile Ala Glu Phe Lys Arg Lys His Lys Lys Asp Ile Ser Glu Asn
                245                 250                 255

Lys Arg Ala Val Arg Arg Leu Arg Thr Ala Cys Glu Arg Ala Lys Arg
                260                 265                 270

Thr Leu Ser Ser Ser Thr Gln Ala Ser Ile Glu Ile Asp Ser Leu Tyr
            275                 280                 285

Glu Gly Ile Asp Phe Tyr Thr Ser Ile Thr Arg Ala Arg Phe Glu Glu
        290                 295                 300

Leu Asn Ala Asp Leu Phe Arg Gly Thr Leu Asp Pro Val Glu Lys Ala
305                 310                 315                 320

Leu Arg Asp Ala Lys Leu Asp Lys Ser Gln Ile His Asp Ile Val Leu
                325                 330                 335

Val Gly Gly Ser Thr Arg Ile Pro Lys Ile Gln Lys Leu Leu Gln Asp
                340                 345                 350

Phe Phe Asn Gly Lys Glu Leu Asn Lys Ser Ile Asn Pro Asp Glu Ala
            355                 360                 365

Val Ala Tyr Gly Ala Ala Val Gln Ala Ala Ile Leu Ser Gly Asp Lys
        370                 375                 380

Ser Glu Asn Val Gln Asp Leu Leu Leu Leu Asp Val Thr Pro Leu Ser
385                 390                 395                 400

Leu Gly Ile Glu Thr Ala Gly Gly Val Met Thr Val Leu Ile Lys Arg
                405                 410                 415

Asn Thr Thr Ile Pro Thr Lys Gln Thr Gln Thr Phe Thr Thr Tyr Ser
                420                 425                 430

Asp Asn Gln Pro Gly Val Leu Ile Gln Val Tyr Glu Gly Glu Arg Ala
            435                 440                 445

Met Thr Lys Asp Asn Asn Leu Leu Gly Lys Phe Glu Leu Thr Gly Met
        450                 455                 460

Pro Gly Gly Met Pro Gly Gly Phe Pro Gly Gly Gly Ala Pro Pro Ser
465                 470                 475                 480

Gly Gly Ala Ser Ser Gly Pro Thr Ile Glu Glu Val Asp
                485                 490
```